(12) United States Patent
Karin et al.

(10) Patent No.: US 6,689,575 B2
(45) Date of Patent: Feb. 10, 2004

(54) IκB KINASE, SUBUNITS THEREOF, AND METHODS OF USING SAME

(75) Inventors: Michael Karin, San Diego, CA (US); Joseph A. DiDonato, Westlake, OH (US); David M. Rothwarf, La Jolla, CA (US); Makio Hayakawa, Tokyo (JP); Ebrahim Zandi, Duarte, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/796,872

(22) Filed: Feb. 28, 2001

(65) Prior Publication Data

US 2002/0045235 A1 Apr. 18, 2002

Related U.S. Application Data

(62) Division of application No. 09/168,629, filed on Oct. 8, 1998, now Pat. No. 6,242,253.
(60) Provisional application No. 60/061,470, filed on Oct. 9, 1997.

(51) Int. Cl.[7] .............................. C12Q 1/48; C12N 9/12; C12N 15/00; G01N 33/53; C07K 1/00
(52) U.S. Cl. ........................ 435/15; 435/194; 435/7.1; 435/325; 435/252.3; 435/320.1; 530/350
(58) Field of Search .............................. 435/194, 320.1, 435/325, 252.3, 15, 7.1; 530/350

(56) References Cited

U.S. PATENT DOCUMENTS

| | | | |
|---|---|---|---|
| 5,264,563 A | 11/1993 | Huse | 536/25.3 |
| 5,270,163 A | 12/1993 | Gold et al. | 435/6 |
| 5,843,721 A | 12/1998 | Rothe et al. | 435/692 |
| 5,851,812 A | 12/1998 | Goeddel | 435/194 |
| 6,235,512 B1 * | 5/2001 | Rothe et al. | 435/194 |
| 6,258,579 B1 * | 7/2001 | Mercurio et al. | 435/194 |
| 6,268,194 B1 * | 7/2001 | Karin et al. | 435/194 |
| 6,277,813 B1 | 8/2001 | Kelly | 514/2 |
| 6,325,989 B1 | 12/2001 | Duke-Cohan et al. | 424/9.34 |
| 6,399,344 B1 | 6/2002 | Eriksson et al. | 435/190 |
| 6,448,052 B2 | 9/2002 | Yasohara et al. | 435/135 |
| 6,517,834 B1 | 2/2003 | Weinrich et al. | 424/94.5 |

FOREIGN PATENT DOCUMENTS

WO    WO 96/27386    9/1996

OTHER PUBLICATIONS

Baeuerle and Baltimore, "NF–kappa B: ten years after," *Cell* 87:13–20 (1996).
Baldi et al., "Critical role for lysines 21 and 22 in signal–induced, ubiquitin–mediated proteolysis of I kappa B–alpha," *J. Biol Chem* 271:376–9 (1996).
Baldwin, "The NF–kappa B and I kappa B proteins: new discoveries and insights," *Annu Rev Immunol* 14:649–83 (1996).
Brown et al., "Control of I kappa B–alpha proteolysis by site–specific, signal–induced phosphorylation," *Science* 267:1485–8 (1995).
Chen et al., "Site–specific phosphorylation of IkappaBalpha by a novel ubiquitination–dependent protein kinase activity," *Cell* 84–853–62 (1996).
Connelly and Marcu, "CHUK, a new member of the helix–loop–helix and leucine zipper families of interacting proteins, contains a serine–threonine kinase catalytic domain," *Cell Mol Biol Res* 41:537–49 (1995).
DiDonato et al., "Phosphorylation of I kappa B alpha precedes but is not sufficient for its dissociation from NK–kappa B," *Mol Cell Biol* 15:1302–11 (1995).
DiDonato et al., "Mapping of the inducible IkappaB phosphorylation sites that signal its ubiquitination and degradation," *Mol Cell Biol* 16:1295–304 (1996).
DiDonato et al., "A cytokine–responsive IkappaB kinase that activates the transcription factor NF–kappaB," *Nature* 388:548–54 (1997).
Kumar et al., "Double–stranded RNA–dependent protein kinase activates transcription factor NF–kappa B by phosphorylating I kappa B," *Proc Natl Acad Sci USA* 91:6288–92 (1994).
Lee et al., "Activation of the IkappaB alpha kinase complex by MEKK1, a kinase of the JNK pathway," *Cell* 88:213–22 (1997).
Malinin et al., "MAP3K–related kinase involved in NF–kappaB induction by TNF, CD95 and IL–1," *Nature* 385:540–4 (1997).
Maran et al., "Blockage of NF–kappa B signaling by selective ablation of an mRNA target by 2–5A antisense chimeras," *Science* 265:789–92 (1994).
Regnier et al., "Identification and characterization of an IkappaB kinase," *Cell* 90:373–83 (1997).

(List continued on next page.)

*Primary Examiner*—Maryam Monshipouri
(74) *Attorney, Agent, or Firm*—Medlen & Carroll LLP

(57) ABSTRACT

The present invention provides an isolated nucleic acid molecules encoding IκB kinase (IKK) catalytic subunit polypeptides, which are associated with an IKK serine protein kinase that phosphorylates a protein (IκB) that inhibits the activity of the NF-κB transcription factor, vectors comprising such nucleic acid molecules and host cells containing such vectors. In addition, the invention provides nucleotide sequences that can bind to a nucleic acid molecule of the invention, such nucleotide sequences being useful as probes or as antisense molecules. The invention also provides isolated IKK catalytic subunits, which can phosphorylate an IκB protein, and peptide portions of such IKK subunit. In addition, the invention provides anti-IKK antibodies, which specifically bind to an IKK complex or an IKK catalytic subunit, and IKK-binding fragments of such antibodies. The invention further provides methods of substantially purifying an IKK complex, methods of identifying an agent that can alter the association of an IKK complex or an IKK catalytic subunit with a second protein, and methods of identifying proteins that can interact with an IKK complex or an IKK catalytic subunit.

20 Claims, 5 Drawing Sheets-

OTHER PUBLICATIONS

GenBank Accession #R10341 (Apr. 6, 1995).
GenBank Accession #N31134 (Jan. 10, 1996).
GenBank Accession #AA326115 (Apr. 20, 1997).
GenBank Accession #U12473 (May 31, 1996).
GenBank Accession #U22512 (Oct. 3, 1996).
GenBank Accession #U48596 (Jun. 5, 1996).
GenBank Accession #M35663 (Apr. 27, 1993).
GenBank Accession #M55268 (Oct. 30, 1994).
Baldwin (1996) The Annual Reviews of Immunology 14:649–81.
Maniatis (Oct. 31, 1997) "Catalysis by a multiprotein IκB complex," Science 278:818–819.
Zandi et al. (Oct. 17, 1997) "The IκB kinase complex (IKK) contains two kinase subunits, IKKα and IKKβ, necessary for IκB phosphorylation and NF–κB activation," Cell 91:243–252.
Rothwarf et al. (Sep. 17, 1998) "IKK–Γ is an essential regulatory subunit of the IκB kinase complex," Nature 395:297–300.
DiDonato et al. (1997) "A cytokine–responsive IκB kinase that activates the transcription factor NF–κB" Nature 388:548–554.
Mercurio et al. (1997) "IKK–1 and IKK–2: Cytokine–activated IκB kinases essential for NF–κB activation," Science 278:860–866.
Woronicz et al. (1997) "IκB kinase–β: NF–κB activation and complex formation with IκB kinase–α and NIK," Science 278:866–869.
Whiteside and Israel (1997) "IκB proteins: structure, function, and regulation" in "Seminars in Cancer Biology" 8:75–82.

* cited by examiner

```
                             TCGACGGAACCTGAGGCCGCTTGCCCTCCCGCCCC
1                                                                    60
atggagcggccccecggggctgcggccgggcgcgggcgggccctgggagatgcgggagcgg
  M  E  R  P  P  G  L  R  P  G  A  G  G  P  W  E  M  R  E  R
61                                                                  120
ctgggcaccggcggcttcgggaacgtctgtctgtaccagcatcgggaacttgatctcaaa
  L  G  T  G  G  F  G  N  V  C  L  Y  Q  H  R  E  L  D  L  K
121                                                                 180
atagcaattaagtcttgtcgcctagagctaagtaccaaaaacagagaacgatggtgccat
  I  A  A  K  S  C  R  L  E  L  S  T  K  N  R  E  R  W  C  H
181                                                                 240
gaaatccagattatgaagaagttgaaccatgccaatgttgtaaaggcctgtgatgttcct
  E  I  Q  I  M  K  K  L  N  H  A  N  V  V  K  A  C  D  V  P
241                                                                 300
gaagaattgaatatttttgattcatgatgtgcctcttctagcaatggaatactgttctgga
  E  E  L  N  I  L  I  H  D  V  P  L  L  A  M  E  Y  C  S  G
301                                                                 360
ggagatctccgaaagctgctcaacaaaccagaaaattgttgtggacttaaagaaagccag
  G  D  L  R  K  L  L  N  K  P  E  N  C  C  G  L  K  E  S  Q
361                                                                 420
atactttctttactaagtgatataggggtctgggattcgatatttgcatgaaaacaaaatt
  I  L  S  L  L  S  D  I  G  S  G  I  R  Y  L  H  E  N  K  I
421                                                                 480
atacatcgagatctaaaacctgaaaacatagttcttcaggatgttggtggaaagataata
  I  H  R  D  L  K  P  E  N  I  V  L  Q  D  V  G  G  K  I  I
481          (peptide 1)                                            540
cataaaataattgatctgggatatgccaaagatgttgatcaaggaagtctgtgtacatct
  H  K  I  I  D  L  G  Y  A  K  D  V  D  Q  G  S  L  C  T  S
541                                                                 600
tttgtgggaacactgcagtatctggccccagagctctttgagaataagccttacacagcc
  F  V  G  T  L  Q  Y  L  A  P  E  L  F  E  N  K  P  Y  T  A
601                                                                 660
actgttgattattggagctttgggaccatggtatttgaatatattgctggatataggcct
  T  V  D  Y  W  S  F  G  T  M  V  F  E  C  I  A  G  Y  R  P
661                                                                 720
ttttttgcatcatctgcagccatttacctggcatgagaagattaagaagaaggatccaaag
  F  L  H  H  L  Q  P  F  T  W  H  E  K  I  K  K  K  D  P  K
721                                                                 780
tgtatatttgcatgtgaagagatgtcaggagaagttcggtttagtagccatttacctcaa
  C  I  F  A  C  E  E  M  S  G  E  V  R  F  S  S  H  L  P  Q
781                                                                 840
ccaaatagcctttgtagtttaatagtagaacccatggaaaactggctacagttgatgttg
  P  N  S  L  C  S  L  I  V  E  P  M  E  N  W  L  Q  L  M  L
841                                                                 900
aattgggaccctcagcagagaggaggacctgttgaccttactttgaagcagccaagatgt
  N  W  D  P  Q  Q  R  G  G  P  V  D  L  T  L  K  Q  P  R  C
901                                                                 960
tttgtattaatggatcacattttgaatttgaagatagtacacatcctaaatatgacttct
  F  V  L  M  D  H  I  L  N  L  K  I  V  H  I  L  N  M  T  S
961                                                                1020
```

FIG. 1A

```
     gcaaagataatttcttttctgttaccacctgatgaaagtcttcattcactacagtctcgt
      A  K  I  I  S  F  L  L  P  P  D  E  S  L  H  S  L  Q  S  R
1021                                                          1080
     attgagcgtgaaactggaataaatactggttctcaagaacttctttcagagacaggaatt
      I  E  R  E  T  G  I  N  T  G  S  Q  E  L  L  S  E  T  G  I
1081                                                          1140
     tctctggatcctcggaaaccagcctctcaatgtgttctagatggagttagaggctgtgat
      S  L  D  P  R  K  P  A  S  Q  C  V  L  D  G  V  R  G  C  D
1141                                                          1200
     agctatatggtttatttgtttgataaaagtaaaactgtatatgaagggccatttgcttcc
      S  Y  M  V  Y  L  F  D  K  S  K  T  V  Y  E  G  P  F  A  S
1201                                                          1260
     agaagtttatctgattgtgtaaattatattgtacaggacagcaaaatacagcttccaatt
      R  S  L  S  D  C  V  N  Y  I  V  Q  D  S  K  I  Q  L  P  I
1261                                                          1320
     atacagctgcgtaaagtgtgggctgaagcagtgcactatgtgtctggactaaaagaagac
      I  Q  L  R  K  V  W  A  E  A  V  H  Y  V  S  G  L  K  E  D
1321                                                          1380
     tatagcaggctctttcagggacaaagggcagcaatgttaagtcttcttagatataatgct
      Y  S  R  L  F  Q  G  Q  R  A  A  M  L  S  L  L  R  Y  N  A
1381                                                          1440
     aacttaacaaaaatgaagaacactttgatctcagcatcacaacaactgaaagctaaattg
      N  L  T  K  M  K  N  T  L  I  S  A  S  Q  Q  L  K  A  K  L
1441                                                          1500
     gagttttttcacaaaagcattcagcttgacttggagagatacagcgagcagatgacgtat
      E  F  F  H  K  S  I  Q  L  D  L  E  R  Y  S  E  Q  M  T  Y
1501                                                          1560
     gggatatcttcagaaaaaatgctaaaagcatggaaagaaatggaagaaaaggccatccac
      G  I  S  S  E  K  M  L  K  A  W  K  E  M  E  E  K  A  I  H
1561                                                          1620
     tatgctgaggttggtgtcattggatacctggaggatcagattatgtctttgcatgctgaa
      Y  A  E  V  G  V  I  G  Y  L  E  D  Q  I  M  S  L  H  A  E
1621                                                          1680
     atcatggggctacagaagagcccctatggaagacgtcagggagacttgatggaatctctg
      I  M  G  L  Q  K  S  P  Y  G  R  R  Q  G  D  L  M  E  S  L
1681                                                          1740
     gaacagcgtgccattgatctatataagcagttaaaacacagaccttcagatcactcctac
      E  Q  R  A  I  D  L  Y  K  Q  L  K  H  R  P  S  D  H  S  Y
1741                                                          1800
     agtgacagcacagagatggtgaaaatcattgtgcacactgtgcagagtcaggaccgtgtg
      S  D  S  T  E  M  V  K  I  I  V  H  T  V  Q  S  Q  D  R  V
1801                                                          1860
     ctcaaggagctgtttggtcatttgagcaagttgttgggctgtaagcagaagattattgat
      L  K  E  L  F  G  H  L  S  K  L  L  G  C  K  Q  K  I  I  D
                                                (peptide 2) 1920
1861
     ctactccctaaggtggaagtggccctcagtattatcaaagaagctgacaatactgtcatg
      L  L  P  K  V  E  V  A  L  S  N  I  K  E  A  D  N  T  V  M
1921                                                          1980
     ttcatgcagggaaaaaggcagaaagaaatatggcatctccttaaaattgcctgtacacag
      F  M  Q  G  K  R  Q  K  E  I  W  H  L  L  K  I  A  C  T  Q
1981                                                          2040
     agttctgcccgctcccttgtaggatccagtctagaaggtgcagtaacccctcagacatca
      S  S  A  R  S  L  V  G  S  S  L  E  G  A  V  T  P  Q  T  S
```

FIG. 1B

```
2041                                                          2100
gcatggctgcccccgacttcagcagaacatgatcattctctgtcatgtgtggtaactcct
 A  W  L  P  P  T  S  A  E  H  D  H  S  L  S  C  V  V  T  P
2101                                                          2160
caagatggggagacttcagcacaaatgatagaagaaaatttgaactgccttggccattta
 Q  D  G  E  T  S  A  Q  M  I  E  E  N  L  N  C  L  G  H  L
2161                                                          2220
agcactattattcatgaggcaaatgaggaacagggcaatagtatgatgaatcttgattgg
 S  T  I  I  H  E  A  M  E  E  Q  G  N  S  M  M  N  L  D  W agttggttaacagaatga
 S  W  L  T  E  *
2221            2238
```

FIG. 1 C

```
   1 CGCGTCCCTG CCGACAGAGT TAGCACGACA TCAGTATGAG CTGGTCACCT TCCCTGACAA
  61 CGCAGACATG CGGGGCCTGG GAAATGAAAG AGCGCCTTGG GACAGGGGGA TTTGGAAATG
 121 TCATCCGATG GCACAATCAG GAAACAGGTG AGCAGATTGC CATCAAGCAG TGCCGGCAGG
 181 AGCTCAGCCC CCGGAACCGA GAGCGGTGGT GCCTGGAGAT CCAGATCATG AGAAGGCTGA
 241 CCCACCCCAA TGTGGTGGCT GCCCGAGATG TCCCTGAGGG GATGCAGAAC TTGGCGCCCA
 301 ATGACCTGCC CCTGCTGGCC ATGGAGTACT GCCAAGGAGG AGATCGCCGG AAGTACCTGA
 361 ACCAGTTTGA GAACTGCTGT GGTCTGCGGG AAGGTGCCAT CCTCACCTTG CTGAGTGACA
 421 TTGCCTCTGC GCTTAGATAC CTTCATGAAA ACAGAATCAT CCATCGGGAT CTAAAGCCAG
 481 AAAACATCGT CCTGCAGCAA GGAGAACAGA GGTTAATACA CAAAATTATT GACCTAGGAT
 541 ATGCCAAGGA GCTGGATCAG GGCAGTCTTT GCACATCATT CGTGGGGACC CTGCAGTACC
 601 TGGCCCCAGA GCTACTGGAG CAGCAGAAGT ACACAGTGAC CGTCGACTAC TGGAGCTTCG
 661 GCACCCTGGC CTTTGAGTGC ATCACGGGCT TCCGGCCCTT CCTCCCCAAC TGGCAGCCCG
 721 TGCAGTGGCA TTCAAAAGTG CGGCAGAAGA GTGAGGTGGA CATTGTTGTT AGCGAAGACT
 781 TGAATGGAAC GGTGAAGTTT TCAAGCTCTT TACCCTACCC CAATAATCTT AACAGTGTCC
 841 TGGCTGAGCG ACTGGAGAAG TGGCTGCAAC TGATGCTGAT GTGGCACCCC CGACAGAGGG
 901 GCACGGATCC CACGTATGGG CCCAATGGCT GCTTCAAGGC CCTGGATGAC ATCTTAAACT
 961 TAAAGCTGGT TCATATCTTG AACATGGTCA CGGGCACCAT CCACACCTAC CCTGTGACAG
1021 AGGATGAGAG TCTGCAGAGC TTGAAGGCCA GAATCCAACA GGACACGGGC ATCCCAGAGG
1081 AGGACCAGGA GCTGCTGCAG GAAGCGGGCC TGGCGTTGAT CCCCGATAAG CCTGCCACTC
1141 AGTGTATTTC AGACGGCAAG TTAAATGAGG CCACACATT GGACATGGAT CTTGTTTTTC
1201 TCTTTGACAA CAGTAAAATC ACCTATGAGA CTCAGATCTC CCCACGGCCC CAACCTGAAA
1261 GTGTCAGCTG TATCCTTCAA GAGCCCAAGA GGAATCTCGC CTTCTTCCAG CTGAGGAAGG
1321 TGTGGGGCCA GGTCTGGCAC AGCATCCAGA CCCTGAAGGA AGATTGCAAC CGGCTGCAGC
1381 AGGGACAGCG AGCCGCCATG ATGAATCTCC TCCGAAACAA CAGCTGCCTC TCCAAAATGA
1441 AGAATTCCAT GGCTTCCATG TCTCAGCAGC TCAAGGCCAA GTTGGATTTC TTCAAAACCA
1501 GCATCCAGAT TGACCTGGAG AAGTACAGCG AGCAAACCGA GTTTGGGATC ACAGCAGATA
1561 AACTGCTGCT GGCCTGGAGG GAAATGGAGC AGGCTGTGGA GCTCTGTGGG CGGGAGAACG
1621 AAGTGAAACT CCTGGTAGAA CGGATGATGG CTCTGCAGAC CCACATTGTG GACTTACAGA
1681 GGAGCCCCAT GGGCCGGAAG CAGGGGGGAA CGCTGGACGA CCTAGAGGAG CAAGCAAGGG
1741 AGCTGTACAG GAGACTAAGG GAAAAACCTC GAGACCAGCG AACTGAGGGT GACAGTCAGG
1801 AAATGGTACG GCTGCTGCTT CAGGCAATTC AGAGCTTCGA GAAGAAAGTG CGAGTGATCT
1861 ATACGCAGCT CAGTAAAACT GTGGTTTGCA AGCAGAAGGC GCTGGAACTG TTGCCCAAGG
1921 TGGAAGAGGT GGTGAGCTTA ATGAATGAGG ATGAGAAGAC TGTTGTCCGG CTGCAGGAGA
1981 AGCGGCAGAA GGAGCTCTGG AATCTCCTGA AGATTGCTTG TAGCAAGGTC CGTGGTCCTG
2041 TCAGTGGAAG CCCGGATAGC ATGAATGCCT CTCGACTTAG CCAGCCTGGG CAGCTGATGT
2101 CTCAGCCCTC CACGGCCTCC AACAGCTTAC CTGAGCCAGC CAAGAAGAGT GAAGAACTGG
2161 TGGCTGAAGC ACATAACCTC TGCACCCTGC TAGAAAATGC CATACAGGAC ACTGTGAGGG
2221 AACAAGACCA GAGTTTCACG GCCCTAGACT GGAGCTGGTT ACAGACGGAA GAAGAAGAGC
2281 ACAGCTGCCT GGAGCAGGCC TCATGATGTG GGGGACTCG ACCCCCTGAC ATGGGGCAGC
2341 CCATAGCAGG CCTTGTGCAG TGGGGGACT CGACCCCCTG ACATGGGCT GCCTGGAGCA
2401 GGCCGCGTGA CGTGGGGCTG CCTGGCCGTG GCTCTCACAT GGTGGTTCCT GCTGCACTGA
2461 TGGCCCAGGG GTCTCTGGTA TCCAGATGGA GCTCTCGCTT CCTCAGCAGC TGTGACTTTC
2521 ACCCAGGACC CAGGACGCAG CCCTCCGTGG GCACTGCCGG CGCCTTGTCT GCACACTGGA
2581 GGTCCTCCAT TACAGAGGCC CAGCGCACAT CGCTGGCCCC ACAAACGTTC AGGGGTACAG
2641 CCATGGCAGC TCCTTCCTCT GCCGTGAGAA AAGTGCTTGG AGTACGGTTT GCCACACACG
2701 TGACTGGACA GTGTCCAATT CAAATCTTTC AGGGCAGAGT CCGAGCAGCG CTTGGTGACA
2761 GCCTGTCCTC TCCTGCTCTC CAAAGGCCCT GCTCCCTGTC CTCTCTCACT TTACAGCTTG
2821 TGTTTCTTCT GGATTCAGCT TCTCCTAAAC AGACAGTTTA ATTATAGTTG CGGCCTGGCC
2881 CCATCCTCAC TTCCTCTTTT TATTTCACTG CTGCTAAAAT TGTGTTTTTA C
```

FIG. 2

```
α  MERPPGLRPGAGGPWEMRERLGTGGFGNVCLYQHRELDLKIAIKSCRLELSTKNRERWCH  60
   |..|:|  ....|:|||:|||||||||||.  ::::| : .|||| ||  |||.:|||||
β  MSWSPSLTTQTCGAWEMKERLGTGGFGNVIRWHNQETGEQIAIKQCRQELSPRNRERWCL  60

α  EIQIMKKLNHANVVKACDVPEEL.NILIHDVPLLAMEYCSGGDLRKLLNKPENCCGLKES  119
   ||||::|.|:||| | ||||::  |:  :|:|||||||||| ||||||.||. ||||||:|:
β  EIQIMRRLTHPNVVAARDVPEGMQNLAPNDLPLLAMEYCQGGDLRKYLNQPENCCGLREG  120

α  QILSLLSDIGSGIRYLHENKIIHRDLKPENIVLQDVGGKIIHKIIDLGYAKDVDQGSLCT  179
   .||.||||:|::|||||||:|||||||||||||||||:..:::|||||||||||::|||||||
β  AILTLLSDIASALRYLHENRIIHRDLKPENIVLQQGEQRLIHKIIDLGYAKELDQGSLCT  180

α  SFVGTLQYLAPELFENKPYTATVDYWSFGTMVPECIAGYRPFLHHLQPFTWHEKIKKKDP  239
   ||||||||||||:|...||.||||||||||:.||||.|:||||.::||. ||.|:::.|..
β  SFVGTLQYLAPELLEQQKYTVTVDYWSFGTLAFECITGFRPFLPNWQPVQWHSKVRQKSE  240

α  KCIPACEEMSGEVRFSSHLPQPNSLCSLIVEPMENWLQLMLNWDPQQRGGPVDLTLKQPR  299
   |...|::.|.|:|||  || ||.| |::.|.:|.|||||| |.|.|||.  ||.
β  VDIVVSEDLNGTVKFSSSLPYPNNLNSVLAERLEKWLQLMLMWHPRQRGT..DPTYGPNG  298

α  CFVLMDHILNLKIVHILNMTSAKIISFLLPPDESLHSLQSRIERETGINTGSQELLSETG  359
   ||  :|.||||||:|||||||..:.|  .:  :..|||||:||..||:.:|||  .:.|||| |.|
β  CEKALDDILNLKLVHILNMVTGTIHTYPVTEDESLQSLKARIQQDTGIPEEDQELLQEAG  358

α  ISLDPRKPASQCV....LDGVRGCDSYMVYLFDKSKTVYEGPPASRSLSDCVNYIVQDSK  415
   :.| | |||.||:   |:..:.   |   :|:|||.||..||..::..|.  ..:|..:|:|.|
β  LALIPDKPATQCISDGKLNEGHTLDMDLVFLFDNSKITYETQISPRPQPESVSCILQEPK  418

α  IQLPIIQLRKVWAEAVHYVSGLKEDYSRLFQGQRAAMLSLLRYNANLTKMKNTLISASQQ  475
   .|:::|||||||::. | : .||||:.||  ||||||||:.||| |. |.|-||||.: | |||
β  RNLAFFQLRKVWGQVWHSIQTLKEDCNRLQQGQRAAMMNLLRNNSCLSKMKNSMASMSQQ  478

α  LKAKLEFFHKSIQLDLERYSEQMTYGISSEKMLKAWKEMEEKAIHYAEVGVIGYLEDQIM  535
   |||||:||..|||:|||:||||   .:||.|:|:| ||:|||: .   ::    . : .| :.:|
β  LKAKLDFFKTSIQIDLEKYSEQTEFGITSDKLLLAWREMEQAVELCGRENEVKLLVERMM  538

α  SLHAEIMGLQKSPYGRRQGDLMESLEQRAIDLYQLKHRPSDG.SYSDSTEMVKIIVHTV  594
   .|::|::||:|| ||:||: ::|||:| :||:.|:.|.|: . :|| |||::::::.:
β  ALQTDIVDLQRSPMGRKQGGTLDDLEEQARELTRRLREKPRDQRTEGDSQEMVRLLLQAI  598

α  QSQDRVLKELFGHLSKLLGCKQKIIDLLPKVEVALSNIKEADNTVMFMQGKRQKEIWHLL  654
   ||  :: ::  ::.:|||  :.||||  ::|||||||  .:|  :.|.:.||   :|:|||||:|:||
β  QSFEKKVRVIYTQLSKTVVCKQKALELLPKVEEVVSLMNEDEKTVVRLQEKRQKELWNLL  658

α  KIACTQSSARSLVGSSLEGAVTPQTSAWLPPTSAEHDHSLSCVVTPQDGETSAQMIEENL  714
   ||||  |..|: |:::| ::    | .|. :.| .: |:..:..|:::.|.
β  KIAC..SKVRGPVSGSPDSMNASRLS...QPGQLMSQPSTASNSLPEPAKKSEELVAEAH  713

α  NCLGHLSTIIHEANEEQGNSMMNLDWSWLTE............  745
   |  . |.. |:::. ||:.|: .|||||| .
β  NLCTLLENAIQDTVREQDQSFTALDWSWLQTEEEEHSCLEQAS  756
```

FIG. 3

IκB KINASE, SUBUNITS THEREOF, AND METHODS OF USING SAME

This is a Divisional of U.S. patent application Ser. No. 09/168,629, filed Oct. 8, 1998 now U.S. Pat. No. 6,242,253, which claim the benefit of, U.S. Provisional Application No. 60/061,470, filed Oct. 9, 1997, the entire contents of which is herein incorporated by reference.

This invention was made with government support under grant number CA50528 awarded by the National Institutes of Health. The government has certain rights in the invention.

BACKGROUND OF THE INVENTION

1. Field of the Invention

The present invention relates generally to molecular biology and biochemistry and more specifically to a protein kinase, IκB kinase, which is activated in response to environmental stresses and proinflammatory signals to phosphorylate inhibitors of the NF-κB transcription factors and to methods of using the protein kinase.

2. Background Information

The induction of gene expression due to exposure of a cell to a specific stimulus is a tightly controlled process. Depending on the inducing stimulus, it can be critical to survival of the cell that one or more genes be rapidly induced, such that the expressed gene product can mediate its effect. For example, an inflammatory response stimulated due to an injury to or infection of a tissue results in rapid vasodilation in the area of the injury and infiltration of effector cells such as macrophages. Vasodilation occurs within minutes of the response and is due, in part, to the expression of cytokines in the injured region.

The rapid induction, for example, of an inflammatory response or an immune response, requires that the transcription factors involved in regulating such responses be present in the cell in a form that is amenable to rapid activation. Thus, upon exposure to an inducing stimulus, the response can occur quickly. If, on the other hand, such transcription factors were not already present in a cell in an inactive state, the factors first would have to be synthesized upon exposure to an inducing stimulus, greatly reducing the speed with which a response such as an inflammatory response could occur.

Regulation of the activity of transcription factors involved in such rapid induction of gene expression can occur by various mechanisms. For example, in some cases, a transcription factor that exists in an inactive state in a cell can be activated by a post-translational modification such as phosphorylation on one or more serine, threonine or tyrosine residues. In addition, a transcription factor can be inactive due to an association with a regulatory factor, which, upon exposure to an inducing stimulus, is released from the transcription factor, thereby activating the transcription factor. Alternatively, an inactive transcription factor may have to associate with a second protein in order to have transcriptional activity.

Rarely, as in the case of glucocorticoids, the inducing stimulus interacts directly with the inactive transcription factor, rendering it active and resulting in the induction of gene expression. More often, however, an inducing stimulus initiates the induced response by interacting with a specific receptor present on the cell membrane or by entering the cell and interacting with an intracellular protein. Furthermore, the signal generally is transmitted along a pathway, for example, from the cell membrane to the nucleus, due to a series of interactions of proteins. Such signal transduction pathways allow for the rapid transmission of an extracellular inducing stimulus such that the appropriate gene expression is rapidly induced.

Although the existence of signal transduction pathways has long been recognized and many of the cellular factors involved in such pathways have been described, the pathways responsible for the expression of many critical responses, including the inflammatory response and immune response, have not been completely defined. For example, it is recognized that various inducing stimuli such as bacteria or viruses activate common arms of the immune and inflammatory responses. However, differences in the gene products expressed also are observed, indicating that these stimuli share certain signal transduction pathways but also induce other pathways unique to the inducing stimulus. Furthermore, since inducing agents such as bacteria or viruses initially stimulate different signal transduction pathways, yet induce the expression of common genes, some signal transduction pathways must converge at a point such that the different pathways activate common transcription factors.

A clearer understanding of the proteins involved in such pathways can allow a description, for example, of the mechanism of action of a drug that is known to interfere with the expression of genes regulated by a particular pathway, but the target of which is not known. In addition, the understanding of such pathways can allow the identification of a defect in the pathway that is associated with a disease such as cancer. For example, the altered expression of cell adhesion molecules is associated with the ability of a cancer cell to metastasize. However, the critical proteins involved in the signal transduction pathway leading to expression of cell adhesion molecules have not been identified. Thus, a need exists to identify the proteins involved in signal transduction pathways, particularly those proteins present at the convergence point of different initial pathways that result in the induction, for example, of gene products involved in the inflammatory and immune responses. The present invention satisfies this need and provides related advantages as well.

SUMMARY OF THE INVENTION

The present invention provides isolated nucleic acid molecules encoding full length human serine protein kinases, designated IκB kinase (IKK) subunits IKKα and IKKβ. The disclosed IKK subunits share substantial sequence homology and are activated in response to proinflammatory signals to phosphorylate proteins (IκB's) that inhibit the activity of the NF-κB transcription factor.

For example, the invention provides a nucleic acid molecule having the nucleotide sequence shown as SEQ ID NO: 1, which encodes a cytokine inducible IκB kinase subunit designated IKKα, particularly the sequence shown as nucleotides −35 to 92 in SEQ ID NO: 1, and nucleic acid molecules encoding the amino acid sequence shown as SEQ ID NO: 2, as well as nucleotide sequences complementary thereto. In addition, the invention provides a nucleic acid molecule having the nucleotide sequence shown as SEQ ID NO: 14, which encodes a second cytokine inducible IκB kinase subunit, designated IKKβ, and nucleic acid molecules encoding the amino acid sequence shown as SEQ ID NO: 15, as well nucleotide sequences complementary thereto. The invention also provides vectors comprising the nucleic acid molecules of the invention and host cells containing such vectors.

In addition, the invention provides nucleotide sequences that bind to a nucleic acid molecule of the invention, including to nucleotides −35 to 92 as shown in SEQ ID NO: 1. Such nucleotide sequences of the invention are useful as probes, which can be used to identify the presence of a nucleic acid molecule encoding an IKK subunit in a sample, and as antisense molecules, which can be used to inhibit the expression of a nucleic acid molecule encoding an IKK subunit.

The present invention also provides isolated full length human IKK subunits, which can phosphorylate an IκB protein. For example, the invention provides an IKKα polypeptide having the amino acid sequence shown as SEQ ID NO: 2, particularly the amino acid sequence comprising amino acids 1 to 31 at the N-terminus of the polypeptide of SEQ ID NO: 2. In addition, the invention provides an IKKβ polypeptide having the amino acid sequence shown as SEQ ID NO: 15. The invention also provides peptide portions of an IKK subunit, including, for example, peptide portions comprising one or more contiguous amino acids of the N-terminal amino acids shown as residues 1 to 31 in SEQ ID NO: 2. A peptide portion of an IKK subunit can comprise the kinase domain of the IKK subunit or can comprise a peptide useful for eliciting production of an antibody that specifically binds to an IκB kinase or to the IKK subunit. Accordingly, the invention also provides anti-IKK antibodies that specifically bind to an IKK complex comprising an IKK subunit, particularly to the IKK subunit, for example, to an epitope comprising at least one of the amino acids shown as residues 1 to 31 of SEQ ID NO: 2, and also provides IKK subunit-binding fragments of such antibodies. In addition, the invention provides cell lines producing anti-IKK antibodies or IKK-binding fragments thereof.

The invention also provides isolated IκB kinase complexes. As disclosed herein, an IKK complex can have an apparent molecular mass of about 900 kDa or about 300 kDa. An IKK complex is characterized, in part, in that it comprises an IKKα subunit, an IKKβ subunit, or both and can phosphorylate an IκB protein.

The present invention further provides methods for isolating an IKK complex or an IKK subunit, as well as methods of identifying an agent that can alter the association of an IKK complex or an IKK subunit with a second protein that associates with the IKK in vitro or in vivo. Such a second protein can be, for example, another IKK subunit; an IκB protein, which is a substrate for IKK activity and is involved in a signal transduction pathway that results in the regulated expression of a gene; a protein that is upstream of the IκB kinase in a signal transduction pathway and regulates IKK activity; or a protein that acts as a regulatory subunit of the IκB kinase or of an IKK subunit and is necessary for full activation of the IKK complex. An agent that alters the association of an IKK subunit with a second protein can be, for example, a peptide, a polypeptide, a peptidomimetic or a small organic molecule. Such agents can be useful for modulating the level of phosphorylation of IκB in a cell, thereby modulating the activity of NF-κB in the cell and the expression of a gene regulated by NF-κB.

The invention also provides methods of identifying proteins that can interact with an IκB kinase, including with an IKK subunit, such proteins which can be a downstream effector of the IKK such as a member of the IκB family of proteins or an upstream activator or a regulatory subunit of an IKK. Such proteins that interact with an IKK complex or the IKK subunit can be isolated, for example, by coprecipitation with the IKK or by using the IKK subunit as a ligand, and can be involved, for example, in tissue specific regulation of NF-κB activation and consequent tissue specific gene expression.

BRIEF DESCRIPTION OF THE DRAWINGS

FIG. 1 shows a nucleotide sequence (SEQ ID NO: 1; lower case letter) and deduced amino acid sequence (SEQ ID NO: 2; upper case letters) of full length human IKKα subunit of an IKK complex. Nucleotide positions are indicated to the right and left of the sequence; the "A" of the ATG encoding the initiator methionine is shown as position 1. Underlined amino acid residues indicate the peptide portions of the protein ("peptide 1" and "peptide 2") that were sequenced and used to design oligonucleotide probes. The asterisk indicates the sequence encoding the STOP codon.

FIG. 2 shows a nucleotide sequence (SEQ ID NO: 14) encoding a full length IKKβ polypeptide (see FIG. 3). Numbers to the left and right of the sequence indicate nucleotide position number. The initiator ATG codon is present at nucleotides 36–38 and the first stop codon (TGA) is present at nucleotides 2304–2306.

FIG. 3 shows an alignment of the deduced amino acid sequences of IKKα ("α", SEQ ID NO: 2) and IKKβ ("β", SEQ ID NO: 15). Numbers to the right of the sequences indicate the respective amino acid positions. Underlined amino acid residues indicate peptide portions of the IKKβ subunit that were sequenced and used to search an EST database (see Example III). Vertical bars between amino acid residues indicate identical amino acids; two dots between amino acid residues indicates very similar amino acids (e.g., Glu and Asp; Arg and Lys) and one dot between amino acid residues indicates a lesser degree of similarity. A dot within an amino acid sequence indicates a space introduced to maintain sequence homology. The kinase domains in the N-terminal half of the sequences and helix-loop-helix domains in the C-terminal half of the sequences are bracketed and the leucine residues involved in the leucine zippers are indicated by the filled circles above the IKKα sequence.

DETAILED DESCRIPTION OF THE INVENTION

The present invention provides isolated nucleic acid molecules encoding polypeptide subunits of human serine protein kinase complex, the IκB kinase (IKK), which is activated in response to proinflammatory signals and phosphorylates proteins (IκB's) that bind to and inhibit the activity of NF-κB transcription factors. For example, the invention provides an isolated nucleic acid molecule (SEQ ID NO: 1) encoding a full length human IKKα subunit having the amino acid sequence shown as SEQ ID NO: 2 (FIG. 1). In addition, the invention provides an isolated nucleic acid molecule (SEQ ID NO: 14; FIG. 2) encoding a full length human IKKβ subunit having the amino acid sequence shown as SEQ ID NO: 15 (FIG. 3).

As used herein, the term "isolated," when used in reference to a nucleic acid molecule of the invention, means that the nucleic acid molecule is relatively free from contaminating lipids, proteins, nucleic acids or other cellular material normally associated with a nucleic acid molecule in a cell. An isolated nucleic acid molecule of the invention can be obtained, for example, by chemical synthesis of the nucleotide sequence shown as SEQ ID NO: 1 or SEQ ID NO: 14 or by cloning the molecule using methods such as those disclosed in Examples II and III. In general, an isolated nucleic acid molecule comprises at least about 30% of a sample containing the nucleic acid molecule, and generally comprises about 50% or 70% or 90% of a sample, preferably 95% or 98% of the sample. Such an isolated nucleic acid molecule can be identified by comparing, for example, a sample containing the isolated nucleic acid molecule with the material from which the sample originally was obtained. Thus, an isolated nucleic acid molecule can be identified, for example, by comparing the relative amount of the nucleic acid molecule in fraction of a cell lysate obtained following gel electrophoresis with the relative amount of the nucleic acid molecule in the cell, itself.

IKKα and IKKβ have been designated IKK subunits because they are components of an approximately 900 kDa complex having IκB kinase (IKK) activity and because they share substantial nucleotide and amino acid sequence homology. As disclosed herein, IKKα and IKKβ are related members of a family of IKK catalytic subunits (see FIG. 3). The 900 kDa IκB kinase complex can be isolated in a single step, for example, by immunoprecipitation using an antibody specific for an IKK subunit or by using metal ion chelation chromatography methods (see Example IV). A 300 kDa IKK complex also can be isolated as disclosed herein and has kinase activity for an IκB substrate (see Example III).

Nucleic acid molecules related to SEQ ID NO: 1 previously have been described (Connelly and Marcu, *Cell. Mol. Biol. Res.* 41:537–549 (1995), which is incorporated herein by reference). For example, Connelly and Marcu describe a 3466 base pair (bp) nucleic acid molecule (GenBank Accession #U12473; Locus MMU 12473), which is incorporated herein by reference), which encodes a full length mouse polypeptide having an apparent molecular mass of 85 kilo-Daltons (kDa) and designated CHUK. A 2146 bp nucleic acid molecule (GenBank Accession #U22512; Locus HSU 22512), which is incorporated herein by reference), which encodes a portion of the polypeptide shown in SEQ ID NO: 2 also was described. However, the amino acid sequence deduced from #U22512 lacks amino acids 1 to 31 as shown in SEQ ID NO: 2 and, therefore, is not a full length protein. In addition, several nucleotide differences occur in SEQ ID NO: 1 as compared to the sequence of #U22512, including nucleotide changes that encode different amino acids at positions 543, 604, 679, 680, 684 and 685 of SEQ ID NO: 2; silent nucleotide changes also occur at codons 665 and 678. The polypeptides encoded by the nucleotide sequences of GenBank Accession #U12473 and #U22512 share about 95% identity at the amino acid level and are substantially similar to that shown in SEQ ID NO: 2. No function has been demonstrated for the polypeptides described by Connelly and Marcu, although Regnier et al. (*Cell* 90:373–383 (1997)) recently have confirmed that human CHUK corresponds to IKKα, as disclosed herein.

A nucleic acid molecule of the invention is exemplified by the nucleotide sequences shown as SEQ ID NO: 1, which encodes a full length human IKKα (SEQ ID NO: 2; FIG. 1), the activity of which is stimulated by a cytokine or other proinflammatory signal, and as SEQ ID NO: 14, which encodes a full length IKKβ (SEQ ID NO: 15). Due to the degeneracy of the genetic code and in view of the disclosed amino acid sequence of a full length human IKKα (SEQ ID NO: 2) and of the IKKβ (SEQ ID NO: 15), additional nucleic acid molecules of the invention would be well known to those skilled in the art. Such nucleic acid molecules, respectively, have a nucleotide sequence that is different from SEQ ID NO: 1 but, nevertheless, encodes the amino acid sequence shown as SEQ ID NO: 2, or have a nucleotide sequence that is different from SEQ ID NO: 14 but, nevertheless, encodes the amino acid sequence shown as SEQ ID NO: 15. Thus, the invention provides a nucleic acid molecule comprising a nucleotide sequence encoding the amino acid sequence of a full length human IKKα as shown in SEQ ID NO: 2 or of IKKβ as shown in SEQ ID NO: 15.

As used herein, reference to "a nucleic acid molecule encoding an IKK subunit" indicates 1) the polynucleotide sequence of one strand of a double stranded DNA molecule comprising the nucleotide sequence that codes for the IKK subunit and can be transcribed into an RNA that encodes the IKK subunit, or 2) an RNA molecule, which can be translated into an IKK subunit. It is recognized that a double stranded DNA molecule also comprises a second polynucleotide strand that is complementary to the coding strand and that the disclosure of a polynucleotide sequence comprising a coding sequence necessarily discloses the complementary polynucleotide sequence. Accordingly, the invention provides polynucleotide sequences, including, for example, polydeoxyribonucleotide or polyribonucleotide sequences that are complementary to the nucleotide sequence shown as SEQ ID NO: 1 or as SEQ ID NO: 14, or to a nucleic acid molecule encoding an IKK catalytic subunit having the amino acid sequence shown as SEQ ID NO: 2 or as SEQ ID NO: 15, respectively.

As used herein, the term "polynucleotide" is used in its broadest sense to mean two or more nucleotides or nucleotide analogs linked by a covalent bond. The term "oligonucleotide" also is used herein to mean two or more nucleotides or nucleotide analogs linked by a covalent bond, although those in the art will recognize that oligonucleotides generally are less than about fifty nucleotides in length and, therefore, are a subset within the broader meaning of the term "polynucleotide."

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can comprise nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997)). The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *BioTechnology* 13:351360 (1995)).

Where it is desired to synthesize a polynucleotide of the invention, the artisan will know that the selection of particular nucleotides or nucleotide analogs and the covalent bond used to link the nucleotides will depend, in part, on the purpose for which the polynucleotide is prepared. For example, where a polynucleotide will be exposed to an environment containing substantial nuclease activity, the artisan will select nucleotide analogs or covalent bonds that are relatively resistant to the nucleases. A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs and, therefore, can be used to produce such a polynucleotide recombinantly from an appropriate template (Jellinek et al., supra, 1995).

The invention also provides nucleotide sequences that can specifically hybridize to a nucleic acid molecule of the invention. Such hybridizing nucleotide sequences are useful, for example, as probes, which can hybridize to a nucleic acid molecule encoding an IKK catalytic subunit and allow the identification of the nucleic acid molecule in a sample. A nucleotide sequence of the invention is characterized, in part, in that it is at least nine nucleotides in length, such sequences being particularly useful as primers for the polymerase chain reaction (PCR), and can be at least fourteen nucleotides in length or, if desired, at least seventeen nucleotides in length, such nucleotide sequences being particularly useful as hybridization probes, although such sequences also can be used for PCR. A nucleotide sequence of the invention can comprise at least six nucleotides 5' to nucleotide position 92 as shown in SEQ ID NO: 1 (FIG. 1), preferably at least nine nucleotides 5' to position 92, or more as desired, where SEQ ID NO: 1 is shown in the conventional manner from the 5'-terminus (FIG. 1; upper left) to the 3'-terminus. Such nucleotide sequences of the invention are particularly useful in methods of diagnosing a pathology, for example, a human disease, characterized by aberrant IKK activity. For convenience, such nucleotide sequences can comprise a kit, which can be made commercially available and can provide a standardized diagnostic assay.

A nucleic acid molecule encoding an IKKα such as the nucleotide sequence shown in SEQ ID NO: 1 diverges from the sequence encoding the mouse homolog (GenBank Accession #U12473) in the region encoding amino acid 30. Thus, a nucleotide sequence comprising nucleotides 88 to 90 as shown in SEQ ID NO: 1, which encodes amino acid 30 of human IKKα, can be particularly useful, for example, for identifying the presence of a nucleic acid molecule encoding a human IKKα in a sample. Furthermore, based on a comparison of SEQ ID NO: 1 with SEQ ID NO: 14, the skilled artisan readily can select nucleotide sequences that can hybridize with a nucleic acid molecule encoding a human IKKα or a human IKKβ or both by designing the sequence to contain conserved or non-conserved nucleotide sequences, as desired. For example, selection of a nucleotide sequence that is highly conserved among SEQ ID NO: 1 and SEQ ID NO: 14 can allow the identification of related members of the IKK subunit family of proteins. In comparison, selection of a nucleotide sequence that is present, for example, in SEQ ID NO: 14, but that is not present in SEQ ID NO: 1 or that shares only minimal homology can allow identification of the expression of SEQ ID NO: 14 in a cell, irrespective of whether SEQ ID NO: 1 also is expressed in the cell. It should be recognized, however, that a nucleotide sequence of the invention readily is identifiable in comparison to GenBank Accession #U12473 or #U22512 in that a nucleotide sequence of the invention is not the nucleotide sequence of GenBank Accession #U12473 or #U22512.

A nucleotide sequence of the invention can comprise a portion of a coding sequence of a nucleic acid molecule encoding an IKK subunit or of a sequence complementary thereto, depending on the purpose for which the nucleotide sequence is to be used. In addition, a mixture of a coding sequence and its complementary sequence can be prepared and, if desired, can be allowed to anneal to produce double stranded molecules.

The invention also provides antisense nucleic acid molecules, which are complementary to a nucleic acid molecule encoding an IKK subunit and can bind to and inhibit the expression of the nucleic acid molecule. As disclosed herein, expression of an antisense molecule complementary to the nucleotide sequence shown in SEQ ID NO: 1 inhibited the cytokine inducible expression of an NF-κB dependent reporter gene in a cell (Example II.B.). Thus, an antisense molecule of the invention can be useful for decreasing IKK activity in a cell, thereby reducing or inhibiting the level of NF-κB mediated gene expression. These experiments were performed twenty-four hours after the cells were transfected (Example II.B.). Expression of the antisense molecule in the cell also resulted in a decreased level of IKKα activity as compared to vector transfected control cells, indicating that the IKKα has a relatively short half life. Antisense nucleic acid molecules specific for IKKα or for IKKβ or for both can be designed based on the criteria discussed above for the selection of hybridizing nucleotide sequences.

An antisense nucleic acid molecule of the invention can comprise a sequence complementary to the entire coding sequence of an IKK catalytic subunit such as a sequence complementary to SEQ ID NO: 1 or SEQ ID NO: 14, provided the antisense sequence is not complementary in its entirety to the sequences of GenBank Accession #U12473 or #U22512. In addition, a nucleotide sequence complementary to a portion of a nucleic acid molecule encoding an IKK subunit can be useful as an antisense molecule, particularly a nucleotide sequence complementary to nucleotides −35 to 92 of SEQ ID NO: 1 or, for example, a nucleotide sequence comprising at least 9 nucleotides on each side of the ATG encoding the initiator methionine (complementary to positions −9 to 12 of SEQ ID NO: 1) or, if desired, at least 17 nucleotides on each side of the ATG codon (complementary to positions −17 to 20 of SEQ ID NO: 1), or to the corresponding sequences of SEQ ID NO: 14.

Antisense methods involve introducing the nucleic acid molecule, which is complementary to and can hybridize to the target nucleic acid molecule, into a cell. An antisense nucleic acid molecule can be a chemically synthesized polynucleotide, which can be introduced into the target cells by methods of transfection, or can be expressed from a plasmid or viral vector, which can be introduced into the cell and stably or transiently expressed using well known methods (see, for example, Sambrook et al., *Molecular Cloning: A laboratory manual* (Cold Spring Harbor Laboratory Press 1989); Ausubel et al., *Current Protocols in Molecular Biology* (Green Publ., NY 1989), each of which is incorporated herein by reference). One in the art would know that the ability of an antisense (or other hybridizing) nucleotide sequence to specifically hybridize to the target nucleic acid sequence depends, for example, on the degree of complementarity shared between the sequences, the GC content of the hybridizing molecules, and the length of the antisense nucleic acid sequence, which can be at least ten nucleotides in length, generally at least thirty nucleotides in length or at least fifty nucleotides in length, and can be up to the full length of a nucleotide sequence of SEQ ID NO: 1 or SEQ ID NO: 14 or a nucleotide sequence encoding an IKK subunit as shown in SEQ ID NO: 2 or in SEQ ID NO: 15 (see Sambrook et al., supra, 1989).

The invention also provides vectors comprising a nucleic acid molecule of the invention and host cells, which are appropriate for maintaining such vectors. Vectors, which can be cloning vectors or expression vectors, are well known in the art and commercially available. An expression vector comprising a nucleic acid molecule of the invention, which can encode an IKK-β or can be an antisense molecule, can be used to express the nucleic acid molecule in a cell.

In general, an expression vector contains the expression elements necessary to achieve, for example, sustained transcription of the nucleic acid molecule, although such elements also can be inherent to the nucleic acid molecule cloned into the vector. In particular, an expression vector contains or encodes a promoter sequence, which can provide constitutive or, if desired, inducible expression of a cloned nucleic acid sequence, a poly-A recognition sequence, and a ribosome recognition site, and can contain other regulatory elements such as an enhancer, which can be tissue specific. The vector also contains elements required for replication in a procaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.*, Vol. 185, D. V. Goeddel, ed. (Academic Press, Inc., 1990); Jolly, *Canc. Gene Ther.* 1:51–64 (1994); Flotte, *J. Bioenerg. Biomemb.* 25:37–42 (1993); Kirshenbaum et al., *J. Clin. Invest* 92:381–387 (1993), which is incorporated herein by reference).

A nucleic acid molecule, including a vector, can be introduced into a cell by any of a variety of methods known in the art (Sambrook et al., supra, 1989, and in Ausubel et al., *Current Protocols in Molecular Biology*, John Wiley and Sons, Baltimore, Md. (1994), which is incorporated herein by reference). Such methods include, for example, transfection, lipofection, microinjection, electroporation and infection with recombinant vectors or the use of liposomes.

Introduction of a nucleic acid molecule by infection with a viral vector is particularly advantageous in that it can efficiently introduce the nucleic acid molecule into a cell ex vivo or in vivo. Moreover, viruses are very specialized and typically infect and propagate in specific cell types. Thus, their natural specificity can be used to target the nucleic acid molecule contained in the vector to specific cell types. For example, a vector based on HIV-1 can be used to target an antisense IKK subunit molecule to HIV-1 infected cells, thereby reducing the phosphorylation of IκB, which can decrease the high level of constitutive NF-κB activity present in HIV-1 infected cells. Viral or non-viral vectors also can be modified with specific receptors or ligands to alter target specificity through receptor mediated events.

A nucleic acid molecule also can be introduced into a cell using methods that do not require the initial introduction of the nucleic acid molecule into a vector. For example, a nucleic acid molecule encoding an IKK catalytic subunit can be introduced into a cell using a cationic liposomes, which also can be modified with specific receptors or ligands as described above (Morishita et al., *J. Clin. Invest.*, 91:2580–2585 (1993), which is incorporated herein by reference; see, also, Nabel et al., supra, 1993)). In addition, a nucleic acid molecule can be introduced into a cell using, for example, adenovirus-polylysine DNA complexes (see, for example, Michael et al., *J. Biol. Chem.*, 268:6866–6869 (1993), which is incorporated herein by reference). Other methods of introducing a nucleic acid molecule into a cell such that the encoded IKK subunit or antisense nucleic acid molecule can be expressed are well known (see, for example, Goeddel, supra, 1990).

Selectable marker genes encoding, for example, a polypeptide conferring neomycin resistance (Neo®) also are readily available and, when linked to a nucleic acid molecule of the invention or incorporated into a vector containing the nucleic acid molecule, allows for the selection of cells that have incorporated the nucleic acid molecule. Other selectable markers such as that conferring hygromycin, puromycin or ZEOCIN (Invitrogen) resistance are known to those in the art of gene transfer can be used to identify cells containing the nucleic acid molecule, including the selectable marker gene.

A "suicide" gene also can be incorporated into a vector so as to allow for selective inducible killing of a cell containing the gene. A gene such as the herpes simplex virus thymidine kinase gene (TK) can be used as a suicide gene to provide for inducible destruction of such cells. For example, where it is desired to terminate the expression of an introduced nucleic acid molecule encoding IKK or an antisense IKK subunit molecule in cells containing the nucleic acid molecule, the cells can be exposed to a drug such as acyclovir or gancyclovir, which can be administered to an individual.

Numerous methods are available for transferring nucleic acid molecules into cultured cells, including the methods described above. In addition, a useful method can be similar to that employed in previous human gene transfer studies, where tumor infiltrating lymphocytes (TILS) were modified by retroviral gene transduction and administered to cancer patients (Rosenberg et al., *New Engl. J. Med.* 323:570–578 (1990)). In that Phase I safety study of retroviral mediated gene transfer, TILs were genetically modified to express the Neomycin resistance (Neo®) gene. Following intravenous infusion, polymerase chain reaction analyses consistently found genetically modified cells in the circulation for as long as two months after administration. No infectious retroviruses were identified in these patients and no side effects due to gene transfer were noted in any patients. These retroviral vectors have been altered to prevent viral replication by the deletion of viral gag, pol and env genes. Such a method can also be used ex vivo to transduce cells taken from a subject (see Anderson et al., U.S. Pat. No. 5,399,346, issued Mar. 21, 1995, which is incorporated herein by reference).

When retroviruses are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. Hence, all retroviral vector supernatants used to infect cells will be screened for replication competent virus by standard assays such as PCR and reverse transcriptase assays.

To function properly, a cell requires the precise regulation of expression of nearly all genes. Such gene regulation is accomplished by activation or repression of transcription by various transcription factors, which interact directly with regulatory sequences on nuclear DNA. The ability of transcription factors to bind DNA or activate or repress transcription is regulated in response to external stimuli. In the case of the transcription factor NF-κB, critical factors involved in the signaling pathway mediating its activation have not been identified (Verma, et al., *Genes Devel.* 9:2723–2735 (1995); Baeuerle and Baltimore, *Cell* 87:13–20 (1996)).

NF-κB is a member of the Rel family of transcription factors, which are present in most if not all animal cells (Thanos and Maniatis, *Cell* 80:629–532 (1995)). Rel proteins, which include, for example, RelA (p65), c-Rel, p50, p52 and the Drosophila dorsal and Dif gene products, are characterized by region of about 300 amino acids sharing approximately 35% to 61% homology ("Rel homology domain"). The Rel homology domain includes DNA binding and dimerization domains and a nuclear localization signal. Rel proteins are grouped into one of two classes, depending on whether the protein also contains a transcriptional activation domain (Siebenlist et al., *Ann. Rev. Cell Biol.* 10:405–455 (1994)).

Rel proteins can from homodimers or heterodimers, which can be transcriptionally activating depending on the presence of a transactivation domain. The most common Rel/NF-κB dimer, which is designated "NF-κB," is a p50/p65 heterodimer that can activate transcription of genes containing the appropriate κB binding sites. p50/p65 NF-κB is present in most cell types and is considered the prototype of the Rel/NF-κB family of transcription factors. Different dimers vary in their binding to different κB elements, kinetics of nuclear translocation and levels of expression in a tissue (Siebenlist et al., supra, 1994). As used herein, the term "Rel/NF-κB" is used to refer generally to the Rel family of transcription factors, and the term "NF-κB" is used to refer specifically to the Rel/NF-κB factor consisting of a p50/p65 heterodimer.

NF-κB originally was identified by its ability to bind a specific DNA sequence present in the immunoglobulin κ light chain gene enhancer, the "κB element" (Sen and Baltimore, *Cell* 46:705–709 (1986)). The κB element has been identified in numerous cellular and viral promoters, including promoters present in human immunodeficiency virus-1 (HIV-1); immunoglobulin superfamily genes such as the MHC class 1 (H-2κ) gene; cytokine genes such as the tumor necrosis factor a (TNFα), interleukin-1β (IL-1β), IL-2, IL-6 and the granulocyte-macrophage colony stimulating factor (GM-CSF) gene; chemokine genes such as RANTES and IL-8; and cell adhesion protein genes such as E-selectin. The κB element exhibits dyad symmetry and each half site of the element likely is bound by one subunit of an NF-κB dimer.

In the absence of an appropriate signaling stimulus, a Rel/NF-κB is maintained in the cytoplasm in an inactive form complexed with an IκB protein. Rel/NF-κB transcriptional activity is induced by numerous pathogenic events or stresses, including cytokines, chemokines, viruses and viral products, double stranded RNA, bacteria and bacterial products such as lipopolysaccharide (LPS) and toxic shock syndrome toxin-1, mitogens such as phorbol esters, physical and oxidative stresses, and chemical agents such as okadaic acid and cycloheximide (Thanos and Maniatis, supra, 1995; Siebenlist et al., supra, 1994). Significantly, the expression of genes encoding agents such as TNFα, IL-1, IL-6, interferon-β and various chemokines, which induce NF-κB activity, are, themselves, induced by NF-κB, resulting in amplification of their signal by a positive, self-regulatory loop (Siebenlist et al., supra, 1994). Phorbol esters, which activate T cells, also activate NF-κB and immunosuppressants such as cyclosporin A inhibit activation of T cells through T cell receptor mediated signals (Baldwin, *Ann. Rev. Immunol.* 14:649–681 (1996), which is incorporated herein by reference).

Regulation of specific genes by NF-κB can require interaction of NF-κB with one or more other DNA binding proteins. For example, expression of E-selectin requires an interaction of NF-κB, the bZIP protein ATF-2 and HMG-I (Y), and expression of the IL-2 receptor α gene requires an interaction of NF-κB, HMG-I(Y) and the ets-like protein, ELF-1 (Baldwin, supra, 1996).

The numerous agents that induce activation of NF-κB likely act through various converging signal transduction pathways, including pathways involving activation of protein kinase C, Raf kinase and tyrosine kinases. The ability of antioxidants to inhibit NF-κB activation by various inducing agents suggests that reactive oxygen species are a converging point of such pathways (Siebenlist et al., supra, 1994).

Upon activation by an appropriate inducing agent, a Rel/NF-κB dimer is translocated into the nucleus, where it can activate gene transcription. The subcellular localization of a Rel/NF-κB is controlled by specific inhibitory proteins ("inhibitors of Rel/NF-κB" or "IκB's"), which noncovalently bind the Rel/NF-κB and mask its nuclear localization signal (NLS), thereby preventing nuclear uptake. Various IκB's, including, for example, IκBα, IκBβ, Bcl-3 and the Drosophila cactus gene product, have been identified (Baeuerle and Baltimore, supra, 1996). In addition, Rel precursor proteins, such as p105 and p100, which are precursors of p50 and p52, respectively, function as IκB's (Siebenlist et al., supra, 1994). IκBα and IκBβ are expressed in most cell types and generally bind p65- and c-Rel-containing Rel/NF-κB dimers. Other IκB's appear to be expressed in a tissue specific manner (Thompson et al., *Cell* 80:573–582 (1995)).

IκB proteins are characterized by the presence of 5 to 8 ankyrin repeat domains, each about 30 amino acids, and a C-terminal PEST domain. For example, IκBβ contains a 70 amino acid N-terminal domain, a 205 amino acid internal domain containing the ankyrin repeats, and a 42 amino acid C-terminal domain containing the PEST domain (Baldwin, supra, 1996). Although IκB proteins interact through their ankyrin repeats with the Rel homology domain of Rel/NF-κB dimers, binding of particular IκB proteins with particular Rel/NF-κB proteins appears to be relatively specific. For example, IκBα and IκBβ associate primarily with RelA- and c-Rel-containing Rel/NF-κB dimers, thereby blocking their nuclear localization signal. The binding of an IκB to NF-κB also interferes with the ability of NF-κB to bind DNA. However, whereas IκBα is phosphorylated following exposure of cells to tumor necrosis factor (TNF), IL-1, bacterial lipopolysaccharide (LPS) or phorbol esters, IκBβ is phosphorylated in certain cell types only in response to LPS or IL-1 (Baldwin, supra, 1996). However, in other cell types, IκBβ is phosphorylated in response to the same signals that induce IκBα, although with slower kinetics than IκBα (DiDonato et al., *Mol. Cell. Biol.* 16:1295–1304 (1996), which is incorporated herein by reference).

Formation of a complex between an IκB protein and a Rel protein is due to an interaction of the ankyrin domains with a Rel homology domain (Baeuerle and Baltimore, supra, 1996). Upon exposure to an appropriate stimulus, the IκB portion of the complex is rapidly degraded and the Rel/NF-κB portion becomes free to translocate to the cell nucleus. Thus, activation of a Rel/NF-κB does not require de novo protein synthesis and, therefore, occurs extremely rapidly. Consequently, activation of gene expression due to a Rel/NF-κB can be exceptionally rapid and provides an effective means to respond to an external stimulus. Such a rapid response of Rel/NF-κB transcription factors is particularly important since these factors are involved in the regulation of genes involved in the immune, inflammatory and acute phase responses, including responses to viral and bacterial infections and to various stresses.

Upon exposure of a cell to an appropriate inducing agent, IκBα, for example, is phosphorylated at serine residue 32 (Ser-32) and Ser-36 (Haskill et al., *Cell* 65:1281–1289 (1991)). Phosphorylation of IκBα triggers its rapid ubiquitination, which results in proteasome-mediated degradation of the inhibitor and translocation of active NF-κB to the nucleus (Brown et al., *Science* 267:1485–1488 (1995); Scherer et al., *Proc. Natl. Acad. Sci., USA.* 92:11259–11263 (1995); DiDonato et al., supra, 1996; DiDonato et al., *Mol. Cell. Biol.* 15:1302–1311 (1995); Baldi et al., *J. Biol. Chem.* 271:376–379 (1996)). The same mechanism also accounts for IκBβ degradation (DiDonato et al., supra, 1996).

Rel/NF-κB activation can be transient or persistent, depending on the inducing agent and the IκB that is phosphorylated. For example, exposure of a cell to particular cytokines induces IκBα phosphorylation and degradation, resulting in NF-κB activation, which induces the expression of various genes, including the gene encoding IκBα. The newly expressed IκBα then binds to NF-κB in the nucleus, resulting in its export to the cytoplasm and inactivation and, therefore, a transient NF-κB mediated response. In comparison, bacterial LPS induces IκBβ phosphorylation, resulting in NF-κB activation. However, the IκBβ gene is not induced by NF-κB and, as a result, activation of NF-κB is more persistent (Thompson et al., supra, 1995).

A constitutively active multisubunit kinase of approximately 700 kDa phosphorylates IκBα at Ser-32 and Ser-36 and, in some cases, requires polyubiquitination for activity (Chen et al., *Cell* 84:853–862 (1996); Lee et al., *Cell* 88:213–222 (1997)). The mitogen-activated protein kinase/ERK kinase kinase-1 (MEKK1) phosphorylates several proteins that copurify with this complex and have molecular weights of approximately 105 kDa, 64 kDa and 54 kDa; three other copurifying proteins having molecular weights of about 200 kDa, 180 kDa and 120 kDa are phosphorylated in the absence of MEKK1 (Lee et al., supra, 1997). However, a catalytically inactive MEKK1 mutant, which can block TNFα mediated activation of the jun kinase, does not block NF-κB activation (Liu et al., *Cell* 87:565–576 (1996)).

Overexpression of MEKK1 also induces the site-specific phosphorylation of IκBα in vivo and can directly activate IκBα in vitro by an ubiquitin-independent mechanism. However, MEKK1 did not phosphorylate IκBα at Ser-32 and Ser-36 in the in vitro experiments, indicating that it is not an IκBα kinase, but may act upstream of IκBβ kinase in a signal transduction pathway (Lee et al., supra, 1997).

In addition to the above described ubiquitin dependent kinase 700 kDa complex, an ubiquitin independent 700 kDa complex, as well as an ubiquitin independent 300 kDa kinase complex phosphorylates IκBα Ser-32 and Ser-36, but not a mutant containing threonines substituted for these serines (Baeuerle and Baltimore, supra, 1996). The specific polypeptides responsible for the IκB kinase activity of these complexes have not been described.

A double stranded RNA-dependent protein kinase (PKR) that phosphorylates IκBα in vitro has been described (Kumar et al., *Proc. Natl. Acad. Sci., USA* 91:6288–6292 (1994)). Moreover, an antisense PKR DNA molecule prevented NF-κB activation by double stranded RNA, but did not prevent NF-κB activation by TNFα (Maran et al., *Science* 265:789–792 (1995)). Casein kinase II (CKII) also can interact with and phosphorylate IκBα, although weakly as compared to CKII phosphorylation of casein, and the Ser-32 and Ser-36 residues in IκBα represent CKII phosphorylation sites (Roulston et al., supra, 1995). However, all of the inducers of NF-κB activity do not stimulate these protein kinases to phosphorylate IκB, indicating that, if they are involved in NF-κB activation, these kinases, like MEKK1, operate upstream of the IκB kinase. Thus, a rapidly stimulated IκB kinase that directly phosphorylates IκBα on Ser-32 and Ser-36 and results in activation of NF-κB has not been identified.

A putative serine-threonine protein kinase has been identified in mouse cells by probing for nucleic acid molecules that encode proteins containing a consensus helix-loop-helix domain, which is involved in protein—protein interactions (Connelly and Marcu, supra, 1995). This putative kinase, which is ubiquitously expressed in various established cell lines, but differentially expressed in normal mouse tissues, was named CHUK (conserved helix-loop-helix ubiquitous kinase; GenBank Accession #U12473). In addition, a nucleic acid molecule (GenBank Accession #U22512) encoding a portion of a human CHUK protein that is 93% identical at the nucleotide level (95% identical at the amino acid level) with the mouse CHUK also was identified. However, neither the function of a CHUK protein in a cell nor a potential substrate for the putative kinase was described.

The present invention provides an isolated IκB kinase (IKK), including isolated full length IKK catalytic subunits. For example, the invention provides an isolated 300 kDa or 900 kDa complex, which comprises an IKKα or an IKKβ subunit and has IκB kinase activity (see Examples I, III and IV). In addition, the invention provides is an isolated human IKKα catalytic subunit (SEQ ID NO: 2; Example II), which contains a previously undescribed N-terminal amino acid sequence and essentially the C-terminal region of human CHUK (Connelly and Marcu, supra, 1995) and phosphorylates IκBα on Ser-32 and Ser-36 and IκBβ on Ser-19 and Ser-23 (DiDonato et al., supra, 1996; see, also, Regnier et al., supra, 1997). The invention also provides an isolated IKKβ catalytic subunit (SEQ ID NO: 15; Example III), which shares greater than 50% amino acid sequence identity with IKKα, including conserved homology in the kinase domain, helix-loop-helix domain and leucine zipper domain.

As used herein, the term "isolated," when used in reference to an IκB kinase complex or to an IKK catalytic subunit of the invention, means that the complex or the subunit is relatively free from contaminating lipids, proteins, nucleic acids or other cellular material normally associated with an IKK in a cell. An isolated 900 kDa IκB kinase complex or 300 kDa complex can be isolated, for example, by immunoprecipitation using an antibody that binds to an IKK catalytic subunit (see Examples III and IV). In addition, an isolated IKK subunit can be obtained, for example, by expression of a recombinant nucleic acid molecule such as SEQ ID NO: 1 or SEQ ID NO: 14, or can be isolated from a cell by a method comprising affinity chromatography using ATP or IκB as ligands (Example I) or using an anti-IKK subunit antibody. An isolated IKK complex or IKK subunit comprises at least 30% of the material in a sample, generally about 50% or 70% or 90% of a sample, and preferably about 95% or 98% of a sample, as described above with respect to nucleic acids.

The amino acid sequences for MEKK1 (GenBank Accession #U48596; locus RNU48596), PKR (GenBank Accession #M35663; locus HUMP68A) and CKII (GenBank Accession #M55268 J02924; locus HUMA1CKII) are different from the sequences of the IKK subunits disclosed herein (SEQ ID NO: 2 and SEQ ID NO: 15) and, therefore, are distinguishable from the present invention. In addition, a full length human IKKα of the invention is distinguishable from the partial human CHUK polypeptide sequence in that the partial human CHUK polypeptide (Connelly and Marcu, supra, 1995; GenBank Accession #22512) lacks amino acids 1 to 31 as shown in SEQ ID NO: 2. As disclosed herein, a polypeptide having the amino acid sequence of the partial human CHUK polypeptide does not have IκB kinase activity when expressed in a cell, indicating that some or all of amino acid residues 1 to 31 are essential for kinase activity.

A full length IKK catalytic subunit of the invention is exemplified by human IKKα, which has an apparent molecular mass of about 85 kDa and phosphorylates IκBα on Ser-32 and Ser-36. An IKK catalytic subunit of the invention also is exemplified by IKKβ, which is an 87 kDa polypeptide that shares substantial amino acid sequence homology with IKKα (FIG. 3). As used herein, the term "full length," when used in reference to an IKK subunit of the invention, means a polypeptide having an amino acid sequence of an IKK subunit expressed normally in a cell. Such a normally expressed IKK polypeptide begins with a methionine residue at its N-terminus (Met-1; FIG. 3), the Met-1 being encoded by the initiator ATG (AUG) codon, and ends as a result of the termination of translation due to the presence of a STOP codon. A full length human IKK catalytic subunit can be a native IKK polypeptide, which is isolated from a cell, or can be produced using recombinant DNA methods such as by expressing the nucleic acid molecule shown as SEQ ID NO: 1 or SEQ ID NO: 14.

The apparent molecular mass of an isolated IKK subunit can be measured using routine methods such as polyacrylamide gel electrophoresis performed in the presence of sodium dodecyl sulfate (SDS-PAGE) or column chromatography performed under reducing and denaturing conditions. In addition, the ability of an IKK subunit to phosphorylate IκBα on Ser-32 and Ser-36 can be identified using the methods disclosed herein.

With regard to the disclosed 85 kDa and 87 kDa apparent molecular masses of human IKKα and IKKβ, it is recognized that the apparent molecular mass of a previously unknown protein as determined, for example, by SDS-PAGE is an estimate based on the relative migration of the unknown protein as compared to the migration of several other proteins having known molecular masses. Thus, one investigator reasonably can estimate, for example, that an unknown protein has an apparent molecular mass of 82 kDa, whereas a second investigator, looking at the same unknown protein under substantially similar conditions, reasonably can estimate that the protein has an apparent molecular mass of 87 kDa. Accordingly, reference herein to an IκB kinase having an apparent molecular mass of "about 85 kDa" indicates that the kinase migrates by SDS-PAGE in an 8% gel under reducing conditions in the range of 80 kDa to 90 kDa, preferably in the range of 82 kDa to 87 kDa. Furthermore, reference herein to an 87 kDa IKKβ indicates that IKKβ has a relatively higher apparent molecular mass than the 85 kDa apparent molecular mass of IKKα.

An IKK catalytic subunit of the invention is exemplified by the isolated full length polypeptide comprising the amino acid sequence shown as SEQ ID NO: 2 or SEQ ID NO: 15. In addition, the invention provides peptide portions of an IKK subunit polypeptide, wherein such peptide portions contain at least three contiguous amino acids as shown in SEQ ID NO: 2 or SEQ ID NO: 15, and generally contain at least six contiguous amino acids or, if desired, at least nine contiguous amino acids, as provided herein. Thus, the invention provides peptide portions of IKKα, containing, for example, at least three contiguous amino acids of SEQ ID NO: 2, including amino acid residue 30, preferably at least four contiguous amino acids, including amino acid residue 30, and more preferably at least six contiguous amino acids, including amino acid residue 30. The invention also provides a peptide portion of IKKβ comprising at least three contiguous amino acids, generally six contiguous amino acids, and preferably ten contiguous amino acids of SEQ ID NO: 15. It is recognized, however, that a peptide of the invention does not consist of a polypeptide disclosed as GenBank Accession #U12473 or #U22512.

A peptide portion of an IKK subunit generally is a tripeptide or larger, preferably a hexapeptide or larger, and more preferably a decapeptide or larger, up to a contiguous amino acid sequence having a maximum length that lacks one or more N-terminal or C-terminal amino acids of the full length polypeptide (SEQ ID NO: 2 or SEQ ID NO: 15). Thus, a peptide portion of IKKα having the amino acid sequence shown as SEQ ID NO: 2 can be from three amino acids long to 744 amino acids long, which is one residue less than the full length polypeptide, except as provided above.

A peptide portion of an IKK subunit polypeptide of the invention can be produced by any of several methods well known in the art. For example, a peptide portion of an IKK subunit can be produced by enzymatic cleavage of an IKK subunit protein, which has been isolated from a cell, using a proteolytic enzyme such as trypsin, chymotrypsin, Lys-C or the like, or combinations of such enzymes. Such proteolytic cleavage products can be isolated using methods as disclosed in Example I, to obtain peptide portions of IKKα and IKKβ, for example. A peptide portion of an IKK subunit also can be produced using methods of solution or solid phase peptide synthesis or can be expressed from a nucleic acid molecule such as a portion of the coding region of the nucleic acid sequence shown as SEQ ID NO: 1 or SEQ ID NO: 14, or can be purchased from a commercial source.

A peptide portion of an IKK subunit can comprise the kinase domain of the IKK subunit and, therefore, can have the ability to phosphorylate an IκB protein. For example, a peptide portion of SEQ ID NO: 2 comprising amino acids 15 to 301 has the characteristics of a serine-threonine protein kinase domain (Hanks and Quinn, *Meth. Enzymol.* 200:38–62 (1991), which is incorporated herein by reference). Such a peptide portion of an IKK subunit can be examined for kinase activity by determining that it can phosphorylate IκBα at Ser-32 and Ser-36 or IκBβ at Ser-19 and Ser-23, using methods as disclosed herein. In addition, a peptide portion of an IKK subunit can comprise an immunogenic amino acid sequence of the polypeptide and, therefore, can be useful for eliciting production of an antibody that can specifically bind the IKK subunit or to an IKK complex comprising the subunit, particularly to an epitope comprising amino acid residue 30 as shown in SEQ ID NO: 2 or to an epitope of SEQ ID NO: 15, provided said epitope is not present in a CHUK protein. Accordingly, the invention also provides anti-IKK antibodies, which specifically bind to an epitope of an IKK complex, particularly an IKK catalytic subunit, and to IKK subunit binding fragments of such antibodies. In addition, the invention provides cell lines producing anti-IKK antibodies or IKK-binding fragments of such antibodies.

As used herein, the term "antibody" is used in its broadest sense to include polyclonal and monoclonal antibodies, as well as antigen binding fragments of such antibodies. With regard to an anti-IKK antibody of the invention, the term "antigen" means an IKK catalytic subunit protein, polypeptide or peptide portion thereof, or an IKK complex comprising an IKK catalytic subunit protein, polypeptide or peptide portion thereof. Thus, it should be recognized that, while an anti-IKK antibody can bind to and, for example, immunoprecipitate an IKK complex, the antibody specifically binds an epitope comprising at least a portion of an IKK catalytic subunit. An antibody of the invention also can be used to immunoprecipitate an IKK subunit, free of the IKK complex.

An anti-IKK antibody, or antigen binding fragment of such an antibody, is characterized by having specific binding activity for an epitope of an IKK subunit of at least about $1 \times 10^5$ M$^{-1}$, generally, at least about $1 \times 10^6$ M$^{-1}$. Thus, Fab, F(aba')$_2$, Fd and Fv fragments of an anti-IKK antibody, which retain specific binding activity for an IKK subunit, are included within the definition of an antibody. In particular, an anti-IKK antibody can react with an epitope comprising the N-terminus of IKKα or with an epitope of IKKβ, but not to a polypeptide having an amino acid sequence shown as residues 32 to 745 of SEQ ID NO: 2.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275–1281 (1989), which is incorporated herein by reference. These and other methods of making, for example, chimeric, humanized, CDR-grafted, single chain, and bifunctional antibodies are well known to those skilled in the art (Winter and Harris, Immunol. Today 14:243–246 (1993); Ward et al., Nature 341:544–546 (1989); Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

An anti-IKK antibody of the invention can be raised using an isolated IKK subunit or a peptide portion thereof and can bind to a free, uncomplexed form of IKK subunit or can bind to IKK subunit when it is associated with a 300 kDa or 900 kDa IKK complex. In addition, an anti-IKK antibody of the invention can be raised against an isolated 300 kDa or 900 kDa IκB kinase complex, which can be obtained as disclosed herein. For convenience, an antibody of the invention is referred to generally herein as an "anti-IκB kinase antibody" or an "anti-IKK antibody." However, the skilled recognize that the various antibodies of the invention will have unique antigenic specificities, for example, for a free or complexed IKK subunit, or both, or for a 300 kDa or 900 kDa IκB kinase complex, or both.

Anti-IKK antibodies can be raised using as an immunogen an isolated full length IKK catalytic subunit, which can be prepared from natural sources or produced recombinantly, or a peptide portion of an IKK subunit as defined herein, including synthetic peptides as described above. A non-immunogenic peptide portion of an IKK catalytic subunit can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane, supra, 1988). It is recognized that, due to the apparently high amino acid sequence identity of the full length human IKKα and mouse CHUK, the amino acid sequences of IKKα polypeptides, as well as IKKβ polypeptides, likely are highly conserved among species, particularly among mammalian species. However, antibodies to highly conserved proteins have been raised successfully, for example, in chickens. Such a method can be used to obtain an antibody to an IKK subunit, if desired.

Particularly useful antibodies of the invention include antibodies that bind with the free, but not the complexed, form of an IKK subunit or, alternatively, with the complexed, but not free, form of an IKK subunit. Antibodies of the invention also include antibodies that bind with the 300 kDa IκB kinase complex or the 900 kDa IκB kinase complex or both. It should be recognized, however, that an antibody specific for the 300 kDa or 900 kDa IκB kinase complex need not recognize an IKK subunit epitope in order to be encompassed within the claimed invention, since, prior to the present disclosure, the 300 kDa and 900 kDa IKK complexes were not known (see DiDonato et al., Nature 388:548–554 (1997)).

Antibodies of the invention that bind to an activated IKK but not to an inactive IKK, and, conversely, those that bind to an inactive form of the kinase but not to the activated form also are particularly useful. For example, an IKK can be activated by phosphorylation of an IKK subunit and, therefore, an antibody that recognizes the phosphorylated form of the IKK, but that does not bind to the unphosphorylated form can be obtained. In addition, IKK can be activated by release of a regulatory subunit and, therefore, an antibody that recognizes a form of the IKK complex that is not bound to the regulatory subunit can be obtained. Such antibodies are useful for identifying the presence of active IKK in a cell.

An anti-IKK antibody is useful, for example, for determining the presence or level of an IKK or of an IKK subunit in a tissue sample, which can be a lysate or a histological section. The identification of the presence or level of an IKK or an IKK subunit in the sample can be made using well known immunoassay and immunohistochemical methods (Harlow and Lane, supra, 1988). An anti-IKK antibody also can be used to substantially purify an IκB kinase or an IKK subunit from a sample. In addition, an anti-IKK antibody can be used in a screening assay to identify agents that alter the activity of an IκB kinase.

A kit incorporating an anti-IKK antibody, which can be specific for the active or inactive form of IκB kinase or can bind to an IKK complex or to an IKK subunit, regardless of the activity state, can be particularly useful. Such a kit can contain, in addition to an anti-IKK antibody, a reaction cocktail that provides the proper conditions for performing the assay, control samples that contain known amounts of an IKK or IKK subunit and, if desired, a second antibody specific for the anti-IKK antibody. Such an assay also should include a simple method for detecting the presence or amount of an IKK or an IKK subunit in a sample that is bound to the anti-IKK antibody.

A protein such as anti-IKK antibody, as well as an IKK subunit or a peptide portion thereof, can be labeled so as to be detectable using methods well known in the art (Hermanson, "Bioconjugate Techniques" (Academic Press 1996), which is incorporated herein by reference; Harlow and Lane, 1988; chap. 9). For example, a protein can be labeled with various detectable moieties including a radiolabel, an enzyme, biotin or a fluorochrome. Reagents for labeling a protein such as an anti-IKK antibody can be included in a kit containing the protein or can be purchased separately from a commercial source.

Following contact, for example, of a labeled antibody with a sample such as a tissue homogenate or a histological section of a tissue, specifically bound labeled antibody can be identified by detecting the particular moiety. Alternatively, a labeled second antibody can be used to identify specific binding of an unlabeled anti-IKK antibody.

A second antibody generally will be specific for the particular class of the first antibody. For example, if an anti-IκB kinase antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, which is an anti-IKK antibody, then the sample is contacted with the labeled second antibody, which specifically binds to the anti-IKK antibody and results in a labeled sample.

Methods for raising polyclonal antibodies, for example, in a rabbit, goat, mouse or other mammal, are well known in the art (see Example V). In addition, monoclonal antibodies can be obtained using methods that are well known and routine in the art (Harlow and Lane, supra, 1988). Essentially, spleen cells from a mouse immunized with an IKK complex or an IKK subunit or peptide portion thereof can be fused to an appropriate myeloma cell line such as SP/02 myeloma cells to produce hybridoma cells. Cloned hybridoma cell lines can be screened using a labeled IKK subunit to identify clones that secrete anti-IKK monoclonal antibodies. Hybridomas expressing anti-IKK monoclonal antibodies having a desirable specificity and affinity can be isolated and utilized as a continuous source of the antibodies, which are useful, for example, for preparing standardized kits as described above. Similarly, a recombinant phage that expresses, for example, a single chain anti-IKK also provides a monoclonal antibody that can used for preparing standardized kits.

A monoclonal anti-IKK antibody can be used to prepare anti-idiotypic antibodies, which present an epitope that mimics the epitope recognized by the monoclonal antibody used to prepare the anti-idiotypic antibodies. Where the epitope to which the monoclonal antibody includes, for example, a portion of the IKK catalytic subunit kinase domain, the anti-idiotypic antibody can act as a competitor of IκB and, therefore, can be useful for reducing the level of phosphorylation of IκB and, consequently, the activity of NF-κB.

The present invention further provides methods of identifying an agent that can alter the association of an IKK catalytic subunit with a second protein, which can be an upstream activator, a downstream effector such as IκB, an interacting regulatory protein of the IKK subunit, or an interacting subunit associated with the 300 kDa or 900 kDa IκB kinase complex. As used herein, the term "associate" or "association," when used in reference to an IKK subunit and a second protein means that the IKK subunit and the second protein have a binding affinity for each other such that they form a bound complex in vivo or in vitro, including in a cell in culture or in a reaction comprising substantially purified reagents. For convenience, the term "bind" or "interact" is used interchangeably with the term "associate."

The affinity of binding of an IKK subunit and a second protein such as an IκB or another IKK subunit or other subunit present in an IKK complex is characterized in that it is sufficiently specific such that a bound complex can form in vivo in a cell or can form in vitro under appropriate conditions as disclosed herein. The formation or dissociation of a bound complex can be identified, for example, using the two hybrid assay or demonstrating coimmunoprecipitation of the second protein with the IKK subunit, as disclosed herein, or using other well known methods such as equilibrium dialysis. Methods for distinguishing the specific association of an IKK subunit and a second protein from nonspecific binding to the IKK subunit are known in the art and, generally, include performing the appropriate control experiments to demonstrate the absence of nonspecific protein binding.

As used herein, the term "second protein" refers to a protein that specifically associates with an IKK subunit ("first protein"). Such a second protein is exemplified herein by IκB proteins, including IκBα and IκBβ, which are substrates for IκB kinase activity and are downstream of the IκB kinase in a signal transduction pathway that results in the regulated expression of a gene. In addition, such second proteins are exemplified by the proteins that, together with the IKK subunits, form a 300 kDa or 900 kDa IκB kinase complex, which coimmunoprecipitates using an anti-IKK antibody (see Example IV). Furthermore, since IKK subunits such as IKKα and IKKβ interact with each other to form homodimers or heterodimers, a second protein also can be a second IKK subunit, which can be the same as or different from the "first" protein.

Agents that alter the association of an IKK catalytic subunit and a second protein such as IκB protein or an IKK regulatory subunit can be extremely valuable, for example, for limiting excessive cytokine expression as occurs in an acute phase response by preventing the activation of NF-κB, thereby preventing NF-κB mediated induction of cytokine gene expression. Where, in a drug screening assay of the invention, the second protein is an IκB, the IKK subunit can be any protein involved in IκB kinase activity, including, for example, mouse CHUK (Connelly and Marcu, supra, 1995; GenBank Accession #12473), which, prior to the present disclosure, was not known to have the ability to associate with IκB or to have IκB kinase activity.

In addition, a second protein can be a protein that is upstream of IκB kinase in a signal transduction pathway and associates with the IKK complex, particularly with an IKK catalytic subunit of the IKK complex. Such a second protein, which can be an upstream activator of the IκB kinase, can be identified using routine methods for identifying protein—protein interactions as disclosed herein. Such second proteins can be, for example, MEKK1 or PKR or CKII, each of which has been reported to be involved in a pathway leading to phosphorylation of IκB and activation of NF-κB, but neither of which has the characteristics expected of the common IκB kinase present at the point where the various NF-κB activation pathways converge (see, for example, Lee et al., supra, 1997), or can be the NF-κB-inducing kinase (NIK), which reportedly is upstream from IKK in an NF-κB activation pathway (Regnier et al., supra, 1997; Malinin et al., Nature 385:540–544 (1997)).

A second protein also can be a regulatory protein, which associates with an IKK catalytic subunit in an IKK complex, either constitutively as part of a 300 kDa or 900 kDa complex or in response to activation of a pathway leading to IKK activation. Such a regulatory protein can inhibit or activate IKK activity depending, for example, on whether the regulatory protein is associated with IKK and whether the regulatory protein associates with an IKK catalytic subunit in a free form or as part of an IKK complex. The regulatory protein also can be important for "docking" a catalytic IKK subunit to its substrate. The ability of a regulatory protein to associate with or dissociate from an IKK subunit or IKK complex can depend, for example, on the relative phosphorylation state of the regulatory protein. It is recognized that an upstream activator of IKK also can interact with such a regulatory protein, thereby indirectly inhibiting or activating the IKK.

As disclosed herein, two copurifying proteins were isolated by ATP and IκB affinity chromatography and identified by SDS-PAGE (Example I). Partial amino acid sequences were determined and cDNA molecules encoding the proteins were obtained (see Examples I, II and III). One of the proteins has an apparent molecular mass of 85 kDa. Expression in a cell of a cDNA molecule encoding the 85 kDa protein resulted in increased NF-κB activity following cytokine induction as compared to control cells, whereas expression of the antisense of this cDNA decreased the basal NF-κB activity in the cells and prevented cytokine induction of NF-κB activity. Immunoprecipitation of the 85 kDa protein resulted in isolation of the IKK complex, the kinase activity of which was stimulated rapidly in response to TNF or to IL-1. Based on these functional analyses, the 85 kDa protein was determined to be a component of the 900 kDa IκB kinase complex and has been designated IKKα (SEQ ID NO: 2). The second protein, which copurified with the 85 kDa IκB kinase, has an apparent molecular mass of 87 kDa and shares greater than 50% amino acid sequence identity with IKKα and has been designated IKKβ (SEQ ID NO: 15).

The ability of the 85 kDa and 87 kDa IKK subunits to associate with other proteins such as a regulatory subunit as well as with IκB is suggested, for example, by the presence in the IκB kinase of two different protein binding domains, a helix-loop-helix domain and a leucine zipper domain (see Connelly and Marcu, supra, 1995; see, also, FIG. 3). While the leucine zipper motif mediates homotypic and heterotypic interactions between IKKα and IKKβ, the helix-loop-helix motif serves as a binding site for regulatory proteins necessary for IκB kinase activation.

A screening assay of the invention provides a means to identify an agent that alters the association of an IKK complex or an IKK catalytic subunit with a second protein such as the regulatory subunits discussed above. As used herein, the term "modulate" or "alter" when used in reference to the association of an IKK and a second protein, means that the affinity of the association is increased or decreased with respect to a steady state, control level of association, i.e., in the absence of an agent. Agents that can alter the association of an IKK with a second protein can be useful for modulating the level of phosphorylation of IκB in a cell, which, in turn, modulates the activity of NF-κB in the cell and the expression of a gene regulated by NF-κB. Such an agent can be, for example, an anti-idiotypic antibody as described above, which can inhibit the association of an IKK and IκB. A peptide portion of IκBα comprising amino acids 32 to 36, but containing substitutions for Ser-32 and Ser-36, is another example of such an agent, since the peptide can compete with IκBα binding to IKK, as is the corresponding peptide of IκBβ.

A screening assay of the invention also is useful for identifying agents that directly alter the activity of an IKK. While such an agent can act, for example, by altering the association of an IKK complex or IKK catalytic subunit with a second protein, the agent also can act directly as a specific activator or inhibitor of IKK activity. Specific protein kinase inhibitors include, for example, staurosporin, the heat stable inhibitor of cAMP-dependent protein kinase, and the MLCK inhibitor, which are known in the art and commercially available. A library of molecules based, generally, on such inhibitors or on ATP or adenosine can be screened using an assay of the invention to obtain agents that desirably modulate the activity of an IKK complex or an IKK subunit.

As disclosed herein, IKK activity can be measured by identifying phosphorylation, for example, of IκBα, either directly or using an antibody specific for the Ser-32 and Ser-36 phosphorylated form of IκBα. An antibody that binds to IκBα that is phosphorylated on Ser-32, for example, can be purchased from a commercial source (New England Biolabs; Beverly Mass.). Cultured cells can be exposed to various agents suspected of having the ability to directly alter IKK activity, then aliquots of the cells either are collected or are treated with a proinflammatory stimulus such as a cytokine, and collected. The collected cells are lysed and the kinase is immunoprecipitated using an anti-IKK antibody. A substrate such as IκBα or IκBβ is added to the immunocomplex and the ability of the IKK to phosphorylate the substrate is determined as described above. If desired, the anti-IKK antibody first can be coated onto a plastic surface such as in 96 well plates, then the cell lysate is added to the wells under conditions that allow binding of IKK by the antibody. Following washing of the wells, IKK activity is measured as described above. Such a method is extremely rapid and provides the additional advantage that it can be automated for high through-put assays.

A screening assay of the invention is particularly useful to identify, from among a diverse population of molecules, those agents that modulate the association of an IKK complex or an IKK catalytic subunit and another protein (referred to herein as a "second protein") or that directly alter the activity of IKK. Methods for producing libraries containing diverse populations of molecules, including chemical or biological molecules such as simple or complex organic molecules, peptides, proteins, peptidomimetics, glycoproteins, lipoproteins, polynucleotides, and the like, are well known in the art (Huse, U.S. Pat. No. 5,264,563, issued Nov. 23, 1993; Blondelle et al., *Trends Anal. Chem.* 14:83–92 (1995); York et al., *Science* 274:1520–1522 (1996); Gold et al., *Proc. Natl. Acad. Sci., USA* 94:59–64 (1997); Gold, U.S. Pat. No. 5,270,163, issued Dec. 14, 1993). Such libraries also can be obtained from commercial sources.

Since libraries of diverse molecules can contain as many as $10^{14}$ to $10^{15}$ different molecules, a screening assay of the invention provides a simple means for identifying those agents in the library that can modulate the association of an IKK and a second protein or can alter the activity of an IKK. In particular, a screening assay of the invention can be automated, which allows for high through-put screening of randomly designed libraries of agents to identify those particular agents that can modulate the ability of an IKK and a second protein to associate or that alter the activity of the IKK.

A drug screening assay of the invention utilizes an IKK complex, which can be isolated as disclosed herein; or an IKK subunit, which can be expressed, for example, from a nucleic acid molecule encoding the amino acid sequence shown in SEQ ID NO: 2 or in SEQ ID NO: 15; or can be purified as disclosed herein; or can utilize an IKK subunit fusion protein such as an IKKα-glutathione-S-transferase (GST) or IKKβ-histidine$_6$ (HIS6) fusion protein, wherein the GST or HIS6 is linked to the IKK subunit and comprises a tag (see Example VI). The IKK or IKK subunit fusion protein is characterized, in part, by having an affinity for a solid substrate as well as having the ability to specifically associate with an appropriate second protein such as an IκB protein. For example, when an IKK catalytic subunit is used in a screening assay, the solid substrate can contain a covalently attached anti-IKK antibody, provided that the antibody binds the IKK subunit without interfering with the ability of the IKK subunit to associate with the second protein. Where an IKKα-GST fusion protein, for example, is used in such a screening assay, the solid substrate can contain covalently attached glutathione, which is bound by the GST tag component of the fusion protein. If desired, the IKK subunit or IKK subunit fusion protein can be part of an IKK complex in a drug screening assay of the invention.

A drug screening assay to identify an agent that alters the association of an IKK complex or an IKK subunit and a second protein can be performed by allowing, for example, the IKK complex or IKK subunit, which can be a fusion protein, to bind to the solid support, then adding the second protein, which can be an IκB such as IκBα, and an agent to be tested, under conditions suitable for the association of the IKK and IκBα in the absence of a drug (see Example VI). As appropriate, the IKK can be activated or inactivated as disclosed herein and, typically, the IKK or the second protein is detectably labeled so as to facilitate identification of the association. Control reactions, which contain or lack either, the IKK component, or the IκB protein, or the agent, or which substitute the IκB protein with a second protein that is known not to associate specifically with the IKK, also are performed. Following incubation of the reaction mixture, the amount of IκBα specifically bound to the IKK in the presence of an agent can be determined and compared to the amount of binding in the absence of the agent so that agents that modulate the association can be identified.

An IKK subunit such as IKKα or IKKβ used in a screening assay can be detectably labeled with a radionuclide, a fluorescent label, an enzyme, a peptide epitope or other such moiety, which facilitates a determination of the amount of association in a reaction. By comparing the amount of specific binding of an IKK subunit or an IKK complex and IκB in the presence of an agent as compared to the control level of binding, an agent that increases or decreases the binding of the IKK and the IκB can be identified. In comparison, where a drug screening assay is used to identify an agent that alters the activity of an IKK, the detectable label can be, for example, $\gamma$-$^{32}$P-ATP, and the amount of $^{32}$P-IκB can be detected as a measure of IKK activity. Thus, the drug screening assay provides a rapid and simple method for selecting agents that desirably alter the association of an IKK and a second protein such as an IκB or for altering the activity of an IKK. Such agents can be useful, for example, for modulating the activity of NF-κB in a cell and, therefore, can be useful as medicaments for the treatment of a pathology due, at least in part, to aberrant NF-κB activity.

The method for performing a drug screening assay as disclosed herein also provides a research tool for identifying a target of a drug that is or can be used therapeutically to ameliorate an undesirable inflammatory or immune response, but for which the target of the drug is not known. Cytokine restraining agents, for example, are a class of agents that can alter the level of cytokine expression (U.S. Pat. No. 5,420,109, issued May 30, 1995) and can be used to treat various pathologies, including patho-immunogenic diseases such as rheumatoid arthritis and those induced by exposure to bacterial endotoxin such as occur in septic shock (see, also, WO96/27386, published Sep. 12, 1996).

The specific cellular target upon which a cytokine restraining agent acts has not been reported. However, the myriad of pathologic effects ameliorated by such agents are similar to various pathologies associated with aberrant NF-κB activity, suggesting that cytokine restraining agents may target an effector molecule in a NF-κB signal transduction pathway. Thus, one potential target of a cytokine restraining agent can be an IκB kinase, particularly an IKK catalytic subunit of the kinase. Accordingly, a screening assay of the invention can be used to determine whether a cytokine restraining agent alters the activity of IκB kinase or alters the association of an IKK and a second protein such as IκB. If it is determined that a cytokine restraining agent has such an effect, the screening assay then can be used to screen a library of cytokine regulatory agents to identify those having desirable characteristics, such as those having the highest affinity for the IKK.

The invention also provides a method of obtaining an isolated IKK complex or an IKK catalytic subunit. For example, a 300 kDa or a 900 kDa IKK complex, comprising an IKKα subunit can be isolated from a sample by immunoprecipitation using an anti-IKKα antibody or by tagging the IKKα and using an antibody specific for the tag (see Examples III and IV). In addition, an IKK catalytic subunit can be isolated from a sample by 1) incubating the sample containing the IKK subunit with ATP, which is immobilized on a matrix, under conditions suitable for binding of the IKK subunit to the ATP; 2) obtaining from the immobilized ATP a fraction of the sample containing the IKK subunit; 3) incubating the fraction containing the IKK subunit with an IκB, which is immobilized on a matrix, under conditions suitable for binding of the IKK subunit to the IκB; and 4) obtaining from the immobilized IκB an isolated IKK catalytic subunit. Such a method of isolating an IKK subunit is exemplified herein by the use of ATP affinity chromatography and IκBα affinity chromatography to isolate IKKα or IKKβ from a sample of HeLa cells (see Example I).

The skilled artisan will recognize that a ligand such as ATP or an IκB or an anti-IKK antibody also can be immobilized on various other matrices, including, for example, on magnetic beads, which provide a rapid and simple method of obtaining a fraction containing an ATP-or an IκB-bound IKK complex or IKK subunit or an anti-IκB kinase-bound IKK from the remainder of the sample. Methods for immobilizing a ligand such as ATP or an IκB or an antibody are well known in the art (Haystead et al., Eur. J. Biochem. 214:459–467 (1993), which is incorporated herein by reference; see, also, Hermanson, supra, 1996). Similarly, the artisan will recognize that a sample containing an IKK complex or an IKK subunit can be a cell, tissue or organ sample, which is obtained from an animal, including a mammal such as a human, and prepared as a lysate; or can be a bacterial, insect, yeast or mammalian cell lysate, in which an IKK catalytic subunit is expressed from a recombinant nucleic acid molecule. As disclosed herein, a recombinantly expressed IKKα or IKKβ such as a tagged IKKα or IKKβ associates into an active 300 kDa and 900 kDa IKK complex (see Examples III and IV).

The invention also provides a method of identifying a second protein that associates with an IKK complex, particularly with an IKK subunit. A transcription activation assay such as the yeast two hybrid system is particularly useful for the identification of protein—protein interactions (Fields and Song, Nature 340:245–246 (1989), which is incorporated herein by reference). In addition, the two hybrid assay is useful for the manipulation of protein—protein interaction and, therefore, also is useful in a screening assay to identify agents that modulate the specific interaction.

A transcription activation assay such as the two hybrid assay also can be performed in mammalian cells (Fearon et al., Proc. Natl. Acad. Sci., USA 89:7958–7962 (1992), which is incorporated herein by reference). However, the yeast two hybrid system provides a particularly useful assay due to the ease of working with yeast and the speed with which the assay can be performed. Thus, the invention also provides methods of identifying proteins that can interact with an IKK subunit, including proteins that can act as upstream activators or downstream effectors of IKK activity in a signal transduction pathway mediated by the IKK or proteins that bind to and regulate the activity of the IKK. Such proteins that interact with an IKK catalytic subunit can be involved, for example, in tissue specific regulation of NF-κB activation or constitutive NF-κB activation and consequent gene expression.

The conceptual basis for a transcription activation assay is predicated on the modular nature of transcription factors, which consist of functionally separable DNA-binding and trans-activation domains. When expressed as separate proteins, these two domains fail to mediate gene transcription. However, the ability to activate transcription can be restored if the DNA-binding domain and the trans-activation domain are bridged together through a protein—protein interaction. These domains can be bridged, for example, by expressing the DNA-binding domain and trans-activation domain as fusion proteins (hybrids), where the proteins that are appended to these domains can interact with each other. The protein—protein interaction of the hybrids can bring the DNA-binding and trans-activation domains together to create a transcriptionally competent complex.

One adaptation of the transcription activation assay, the yeast two hybrid system, uses *S. cerevisiae* as a host cell for vectors that express the hybrid proteins. For example, a yeast host cell containing a reporter lacZ gene linked to a LexA operator sequence can be used to identify specific interactions between an IKK subunit and a second protein, where the DNA-binding domain is the LexA binding domain, which binds the LexA promoter, and the trans-activation domain is the B42 acidic region. When the LexA domain is bridged to the B42 transactivation domain through the interaction of the IKK subunit with a second protein, which can be expressed, for example, from a cDNA library, transcription of the reporter lacZ gene is activated. In this way, proteins that interact with the IKK subunit can be identified and their role in a signal transduction pathway mediated by the IKK can be elucidated. Such second proteins can include additional subunits comprising the 300 kDa or 900 kDa IKK complex.

In addition to identifying proteins that were not previously known to interact with an IKK, particularly with an IKKα or IKKβ subunit, a transcription activation assay such as the yeast two hybrid system also is useful as a screening assay to identify agents that alter association of an IKK subunit and a second protein known to bind the IKK. Thus, as described above for in vitro screening assays, a transcription activation assay can be used to screen a panel of agents to identify those agents particularly useful for altering the association of an IKK subunit and a second protein in a cell. Such agents can be identified by detecting an altered level of transcription of a reporter gene, as described above, as compared to the level of transcription in the absence of the agent. For example, an agent that increases the interaction between an IKK subunit and IκB can be identified by an increased level of transcription of the reporter gene as compared to the control level of transcription in the absence of the agent. Such a method is particularly useful because it identifies an agent that alters the association of an IKK subunit and a second protein in a living cell.

In some cases, an agent may not be able to cross the yeast cell wall and, therefore, cannot enter the yeast cell to alter a protein—protein interaction. The use of yeast spheroplasts, which are yeast cells that lack a cell wall, can circumvent this problem (Smith and Corcoran, In *Current Protocols in Molecular Biology* (ed. Ausubel et al.; Green Publ., NY 1989), which is incorporated herein by reference). In addition, an agent, upon entering a cell, may require "activation" by a cellular mechanism that may not be present in yeast. Activation of an agent can include, for example, metabolic processing of the agent or a modification such as phosphorylation of the agent, which can be necessary to confer activity upon the agent. In this case, a mammalian cell line can be used to screen a panel of agents (Fearon et al., supra, 1992).

An agent that alters the catalytic activity of an IKK or that alters the association of an IKK subunit or IKK complex and a second protein such as an IκB or an IKK regulatory subunit or an upstream activator of an IKK can be useful as a drug to reduce the severity of a pathology characterized by aberrant NF-κB activity. For example, a drug that increases the activity of an IKK or that increases the affinity of an IKK catalytic subunit and IκBα can increase the amount of IκBα phosphorylated on Ser-32 or Ser-36 and, therefore, increase the amount of active NF-κB and the expression of a gene regulated by NF-κB, since the drug will increase the level of phosphorylated IκBα in the cell, thereby allowing NF-κB translocation to the nucleus. In contrast, a drug that decreases or inhibits the catalytic activity of an IKK or the association of an IKK catalytic subunit and IκBα can be useful where it is desirable to decrease the level of active NF-κB in a cell and the expression of a gene induced by activated NF-κB. It should be recognized that an antisense IKK subunit molecule of the invention also can be used to decrease IKK activity in a cell by reducing or inhibiting expression of the IKK subunit or by reducing or inhibiting its responsiveness to an inducing agent such as TNFα, Il-1 or phorbol ester (see Example II). Accordingly, the invention also provides methods of treating an individual suffering from a pathology characterized by aberrant NF-κB activity by administering to the individual an agent that modulates the catalytic activity of an IKK or that alters the association of an IKK subunit and a second protein such as IκB or a subunit of a 300 kDa or 900 kDa IKK complex that interacts with the IKK subunit.

An agent that decreases the activity of an IKK or otherwise decreases the amount of IκB phosphorylation in a cell can reduce or inhibit NF-κB mediated gene expression, including, for example, the expression of proinflammatory molecules such as cytokines and other biological effectors involved in an inflammatory, immune or acute phase response. The ability to reduce or inhibit such gene expression can be particularly valuable for treating various pathological conditions such as rheumatoid arthritis, asthma and septic shock, which are characterized or exacerbated by the expression of such proinflammatory molecules.

Glucocorticoids are potent anti-inflammatory and immunosuppressive agents that are used clinically to treat various pathologic conditions, including autoimmune diseases such as rheumatoid arthritis, systemic lupus erythematosis and asthma. Glucocorticoids suppress the immune and inflammatory responses, at least in part, by increasing the rate of IκBα synthesis, resulting in increased cellular levels of IκBα, which bind to and inactivate NF-κB (Scheinman et al., *Science* 270:283–286 (1995); Auphan et al., *Science* 270:286–290 (1995)). Thus, glucocorticoids suppress NF-κB mediated expression of genes encoding, for example, cytokines, thereby suppressing the immune, inflammatory and acute phase responses. However, glucocorticoids and glucocorticoid-like steroids also are produced physiologically and are required for normal growth and development. Unfortunately, prolonged treatment of an individual with higher than physiological amounts of glucocorticoids produces clinically undesirable side effects. Thus, the use of an agent that alters the activity of an IKK or that alters the association of an IKK complex or IKK subunit and a second protein, as identified using a method of the invention, can provide a means for selectively altering NF-κB activity without producing some of the undesirable side effects associated with glucocorticoid treatment.

Inappropriate regulation of Rel/NF-κB transcription factors is associated with various human diseases. For example, many viruses, including human immunodeficiency virus-1 (HIV-1), herpes simplex virus-1 (HSV-1) and cytomegalovirus (CMV) contain genes regulated by a κB regulatory element and these viruses, upon infecting a cell, utilize cellular Rel/NF-κB transcription factors to mediate viral gene expression (Siebenlist et al., supra, 1994). Tat-mediated transcription from the HIV-1 enhancer, for example, is decreased if the NF-κB and SP1 binding sites are deleted from the enhancer/promotor region, indicating that Tat interacts with NF-κB, SP1 or other transcription factors bound at this site to stimulate transcription (Roulston et al., *Microbiol. Rev.* 59:481–505 (1995)). In addition, chronic HIV-1 infection, and progression to AIDS, is associated with the development of constitutive NF-κB DNA binding activity in myeloid cells (Roulston et al., supra, 1995). Thus, a positive autoregulatory loop is formed, whereby HIV-1 infection results in constitutively active NF-κB, which induces expression of HIV-1 genes (Baeuerle and Baltimore, *Cell* 87:13–20 (1996). Constitutive NF-κB activation also may protect cells against apoptosis, preventing clearance of virus-infected cells by the immune system (Liu et al., supra, 1996).

An agent that decreases the activity of an IKK or that alters the association of an IKK and a second protein such that IκB phosphorylation is decreased can be useful for reducing the severity of a viral infection such as HIV-1 infection in an individual by providing increased levels of unphosphorylated IκB in virus-infected cells. The unphosphorylated IκB then can bind to NF-κB in the cell, thereby preventing nuclear translocation of the NF-κB and viral gene expression. In this way, the rate of expansion of the virus population can be limited, thereby providing a therapeutic advantage to the individual.

In addition, the decreased level of NF-κB activity may allow the virus-infected cell to undergo apoptosis, resulting in a decrease in the viral load in the individual. As such, it can be particularly useful to treat virus-infected cells ex vivo with an agent identified using a method of the invention. For example, peripheral blood mononuclear cells (PBMCs) can be collected from an HIV-1 infected individual and treated in culture with an agent that decreases the activity of an IKK or alters the association of an IKK complex or an IKK catalytic subunit with an IκB. Such a treatment can be useful to purge the PBMCs of the virus-infected cells by allowing apoptosis to proceed. The purged population of PBMCs then can be expanded, if desired, and readministered to the individual.

Rel/NF-κB proteins also are involved in a number of different types of cancer. For example, the adhesion of cancer cells to endothelial cells is increased due to treatment of the cancer cells with IL-1, suggesting that NF-κB induced the expression of cell adhesion molecules, which mediated adherence of the tumor cells to the endothelial cells; agents such as aspirin, which decrease NF-κB activity, blocked the adhesion by inhibiting expression of the cell adhesion molecules (Tozawa et al., *Cancer Res.* 55:4162–4167 (1995)). These results indicate that an agent that decreases the activity of an IKK or that decrease the association of an IKK and IκB or of an IKK subunit and a second protein, for example, a second protein present in an IKK complex, can be useful for reducing the likelihood of metastasis of a tumor in an individual.

As discussed above for virus-infected cells, constitutive NF-κB activation also may protect tumor cells against programmed cell death as well as apoptosis induced by chemotherapeutic agents (Liu et al., supra, 1996; Baeuerle and Baltimore, *Cell* 87:13–20 (1996)). Thus, an agent that decreases IKK activity or that decreases the association of IKK and IκB also can be useful for allowing programmed cell death to occur in a tumor cell by increasing the level of unphosphorylated IκB, which can bind NF-κB and decrease the level of active NF-κB in the tumor cell.

The following examples are intended to illustrate but not limit the present invention.

EXAMPLE I

Identification and Characterization of a Human IκB Kinase Complex And IKK Subunits This example provides a method for identifying and isolating a cytokine responsive protein kinase complex that phosphorylates IκB, which regulates NF-κB activity, and catalytic subunits of the protein kinase complex.

A. Kinase assays:

Kinase assays were performed using GST fusion proteins containing amino acid residues 1 to 54 of IκB. The fusion proteins were linked to glutathione SEPHAROSE and the beads were used directly in the assays. At earlier stages in the purification of the IKK activity, the beads were washed prior to loading onto the gel to minimize contributions from other proteins. In some of the later characterization of highly purified material, soluble fusion protein was used.

Three distinct substrates for the IKK activity were used: 1) substrate "WT" contained amino acid residues 1 to 54 of IκBα; 2) substrate "AA" contained amino acid residues 1 to 54 of IκBα, except that Ser-32 (S32) and S36 were replaced with Ala-32 (A32) and A36, respectively; and 3) substrate "TT" contained amino acid residues 1 to 54 of IκBα, except that S32 and S36 were replaced with Thr-32 (T32) and T36, respectively (DiDonato et al., *Mol. Cell. Biol.* 16:1295–1304 (1996)). Each substrate was expressed as a GST fusion protein. The physiologic, inducible IκB kinase is specific for S32 and S36 (WT) in IκBα, but does not recognize the TT or AA mutants (DiDonato et al., *Mol. Cell. Biol.* 16:1295–1304 (1996)).

Kinase assays were carried out in 20 mM HEPES (pH 7.5–7.6), 20 mM β-glycerophosphate (β-GP), 10 mM $MgCl_2$, 10 mM PNPP, 100 μM $Na_3VO_4$, 2 mM dithiothreitol (DTT), 20 μM ATP, 10 μg/ml aprotinin. NaCl concentration was 150–200 mM and the assays were carried out at 30° C. for 30 min. Fractionation was performed by SDS-PAGE, followed by quantitation by phosphoimager analysis.

B. Purification of IKK Complex and IKK Subunits:

The protein purification buffer (Buffer A) consisted of 20 mM Tris (pH 7.6, measured at RT), 20 mM NaF, 20 mM β-GP, 1 mM PNPP, 500 μm $Na_3VO_4$, 2 mM DTT, 2.5 mM metabisulfite, 5 mM benzamidine, 1 mM EDTA, 0.5 mM EGTA, 1 mM PMSF, and 10% glycerol. Brij-35 was added as indicated. Cell lysis buffer was Buffer A containing an additional 19 mM PNPP, 20 mM β-GP and 500 μm $Na_3VO_4$, and 20 μg/ml aprotinin, 2.5 μg/ml leupeptin, 8.3 μg/ml bestatin, 1.7 μg/ml pepstatin.

Purification was performed using 5 to 130 liters of HeLa S3 cells. For illustration, the procedure for a 15 liter preparation is presented. All purification steps were performed in a cold room at 4° C.

In order to activate the IKK, cells were stimulated with TNFα prior to purification. TNFα was either recombinant TNFα, which was purchased from R&D Systems and used at 20 ng/ml, or HIS6-tagged TNFα, which was expressed and partially purified from *E. coli* and used at 5 µg/ml. TNFα-induced HeLa S3 cell killing activity assays were performed in the presence of cycloheximide and indicated that the partially purified HIS6-tagged TNFα had approximately one-tenth the activity of the commercial TNFα.

Fifteen liters of HeLa S3 cells were grown in suspension in high glucose Dulbecco's modified Eagle's medium supplemented with 10% calf serum, 2 mg/ml L-glutamine, 100 U/ml penicillin/streptomycin, 0.11 mg/ml sodium pyruvate, and 1X nonessential amino acids (Irvine Scientific; Irvine Calif.). Cell density was approximately $5 \times 10^5$ cells/ml at the time of collection. Cells were concentrated 10-fold by centrifugation. stimulated for 5 min with TNFα at 37° C., then diluted with 2.5 volumes of ice cold phosphate buffered saline (PBS) containing 50 mM NaF and pelletted at 2000×g. The cell pellet was washed once with ice cold PBS/50 mM NaF, then suspended in lysis buffer, quick frozen in liquid nitrogen and stored at ⁻80° C.

For purification of IκB kinase, cells were thawed and cytoplasmic extract prepared. Lysis was achieved by 40 strokes in an all glass Dounce homogenizer (pestle A) in lysis buffer containing 0.05% NP-40 on ice. The homogenate was centrifuged at 12,000 rpm for 19 min in a Beckman SS34 rotor at 4° C.

Supernatant was collected and centrifuged at 38,000 rpm for 80 min in a Beckman 50.1 Ti rotor at 4° C. The supernatant (S100 fraction) was quick frozen in liquid nitrogen and stored at ⁻80° C. Small aliquots of S100 material, prepared from either unstimulated HeLa cells or from TNFα stimulated cells, were purified in a single passage over a SUPEROSE 6 gel filtration column (1.0×30 cm; Pharmacia; Uppsalla Sweden) equilibrated in Buffer A containing 0.1% Brij-35 and 300 mM NaCl and eluted at a flow rate of 0.3 ml/min. 0.6 ml fractions were collected and kinase assays were performed on an aliquot of each fraction. The high molecular weight material (fractions 16–20) contained TNFα-inducible IKK activity, which is specific for the WT substrate.

110 ml of S100 material (900 mg of protein; Bio-Rad Protein Assay) was pumped onto a Q-SEPHAROSE FAST FLOW column (56 ml bed volume, 2.6 cm ID) equilibrated at 2 ml/min with Buffer A containing 0.1% Brij-35. After the sample was loaded, the column was washed with 100 ml of Buffer A containing 0.1% Brij-35 and 100 mM NaCl, then a linear NaCl gradient was run from 100–300 mM. The gradient volume was 500 ml and the flow rate was 2 ml/min. Ten ml fractions were collected and the kinase assay was performed on those fractions that eluted during the gradient. Fractions corresponding to the TNFα-inducible IKK activity (fractions 30–42; i.e., 20–32 of the gradient portion) were pooled. The pooled material contained 40 mg of protein.

The pooled material was diluted to 390 ml by addition of Buffer A containing 0.1% Brij-35 and loaded onto a pre-equilibrated 5 ml HITRAP Q column (Pharmacia) at a flow rate of 4 ml/min. Following sample loading, the column was washed with 20 ml of Buffer A containing 0.1% Brij-35. The protein was eluted at 1 ml/min isocratically in Buffer A containing 0.1% Brij-35 and 300 mM NaCl and 1 ml fractions were collected. Protein-containing fractions were identified using the BioRad assay and were collected and pooled to yield 4 ml of solution. Previously performed control experiments demonstrated that the IKK activity directly correlated with protein concentration.

The pooled material was diluted 1:1 with ATP column buffer (20 mM HEPES (pH 7.3), 50 mM β-GP, 60 mM MgCl$_2$, 1 mM Na$_2$VO$_4$, 1.5 mM EGTA, 1 mM DTT, 10 µg/ml aprotinin), then passed 4 times over a γ-ATP affinity column having 4 ml bed volume (Haystead et al., supra, 1993); the column had been prewashed with 2 M NaCl, 0.25% Brij-35 and equilibrated with 10 bed volumes of ATP column buffer containing 0.05% Brij-35 at a flow rate of 0.5 ml/min. Following loading of the sample, the column was washed with 10 ml of ATP column buffer containing 0.05% Brij-35, then with 10 ml ATP column buffer containing 0.05% Brij-35 and 250 mM NaCl.

Bound material was eluted in 10 ml of ATP column buffer containing 0.05% Brij-35, 250 mM NaCl and 10 mM ATP (elution buffer). Elution was performed by passing 5 ml of elution buffer through the column, allowing the column to incubate, capped, for 20 min, then passing an additional 5 ml of elution buffer through the column. The samples were pooled to yield 10 ml.

The 10 ml pooled sample from the ATP column was diluted with 30 ml Buffer A containing 0.1% Brij-35 and loaded onto a 1 ml HITRAP Q column (Pharmacia) at 1 ml/min. The column was eluted at 0.4 ml/min with Buffer A containing 0.1% Brij-35 and 300 mM NaCl. 0.2 ml fractions were collected and the four protein-containing fractions were pooled (0.5 mg). The pooled material was concentrated to 200 µl on a 10K NANOSEP concentrator (Pall/Filtron) and loaded onto a SUPEROSE 6 gel filtration column (1.0×30 cm). The SUPEROSE 6 column was equilibrated in Buffer A containing 0.1% Brij-35 and 300 mM NaCl and run at a flow rate of 0.3 ml/min; 0.6 ml fractions were collected. Fractions 17, 18 and 19 contained kinase activity.

Based on silver stained SDS-PAGE gels, the final purified material consisted of approximately 20 µg to 40 µg of total protein, of which approximately 2 µg corresponded to the 85 kDa band, later designated IKKα (see Example II). A second band migrating at 87 kDa was later designated IKKβ (see Example III). The total time from the thawing of the S100 material until the collection of fractions from the gel filtration column was 24 hours.

C. Confirmation of IKK Purification:

Since the 85 kDa IKKα band identified by the kinase assay following the above procedure contained only about 10% of the total purified protein, three additional criteria were used to confirm that the identified band was an intrinsic component of the IKK complex.

In one procedure, the elution profile of the SUPEROSE 6 column was analyzed by silver stained 8% SDS-PAGE gels, then compared to the kinase activity profile. For this analysis, 0.3 ml fractions were collected from the SUPEROSE 6 column, then separated by 8% SDS-PAGE and silver stained. This comparison confirmed that a single band of 85 kDa correlated precisely with the elution of IKK activity.

In a second procedure, the IKK activity was further purified on a substrate affinity column at 4° C. A GST fusion protein was prepared containing the A32/A36 1 to 54 amino acid sequence of IκBα repeated 8 times (GST-(8X-AA)). The GST-(8X-AA) then was covalently linked to a CNBr activated SEPHAROSE 4B resin to produce the substrate affinity resin.

IKK-containing material was diluted into Buffer A to yield a final concentration of 70 mM NaCl, 0.025% Brij-35, then added to the substrate affinity resin at a ratio of 4:1 (solution:swollen beads). The resin was suspended and the mixture rotated gently overnight in a small column at 4° C. The resin was allowed to settle for 30 min, then the column was eluted by gravity. The column was washed with 4 bed volumes Buffer A containing 0.02% Brij-35, then the resin was suspended with 1.1 bed volumes of Buffer A containing 600 mM NaCl and 0.1% Brij-35. The resin was allowed to settle for 40 min, then gravity elution was performed. The column was washed with an additional 1.1 bed volumes of Buffer A containing 600 mM NaCl and 0.1% Brij-35 and the two fractions were pooled.

The IκBα substrate affinity column was used for two separate experiments. In one experiment, the material that eluted from the final SUPEROSE 6 column was further purified on the IκBα substrate affinity column. In the second experiment, material obtained after the initial Q-SEPHAROSE column was purified on the IκBα substrate affinity column. The Q-SEPHAROSE bound fraction then was further purified on the ATP column and the SUPEROSE 6 column (see above).

Analysis of the purified material from these two experiments by silver stained SDS-PAGE gels revealed different protein profiles. However, comparison of these profiles revealed only two bands common to both preparations, one of which was confirmed to be the same 85 kDa IKKα band that was identified by the SUPEROSE 6 profile analysis and cofractionated with IκB kinase activity. The other band, which was 87 kDa in size, later was identified as IKKβ. In several different experiments, the 85 kDa protein and 87 kDa protein were specifically purified by the substrate affinity column in what appeared to be an equimolar ratio.

In a third procedure, purified IKK was treated with excess phosphatase, which inactivates the IKK, then reactivated by addition of a semi-purified HeLa extract. Phosphatase inactivation was performed by adding excess protein phosphatase 2A catalytic domain (PP2A) to purified IκB kinase in 50 mM Tris (pH 7.6), 50 mM NaCl, 1 mM MgCl$_2$, then equilibrating the reaction for 60 min at 30° C. 1.25 µM okadaic acid was added to completely inactivate the phosphatase and the phosphatase inactivated material was used in standard kinase assays and to perform the reactivation and phosphorylation procedure.

Cytoplasmic extract was prepared using HeLa S3 cells. The cells were stimulated with TNFα for 5 min, then harvested in lysis buffer containing 0.1% NP-40 and 0.15 M NaCl. Reactivation was performed at 30° C. in kinase buffer for 60 min in the absence of (γ-$^{32}$P)ATP. Samples containing only cold ATP were used for kinase activity assays. Reactivation by the HeLa cell extract was performed in the presence of (γ-$^{32}$P)ATP, then the sample was separated by 8% SDS-PAGE and examined by autoradiography. A band of approximately 86 kDa was phosphorylated in the reactivated material and, associated with the reactivation procedure, was restoration of the IKK activity.

D. Partial Amino Acid Sequences of IKKα and IKKβ

Following SDS-PAGE as described above, the 85 kDa IKKα and 87 kDa IKKβ bands were excised from the gel and submitted for internal peptide sequencing analysis. From the IKKα polypeptide, the sequences of two proteolytic fragments were identified, as follows: KIIDLLPK (SEQ ID NO: 3) and KHR(D/A)LKPENIVLQDVG(P/G)K (SEQ ID NO: 4). Where a residue could not be unambiguously determined, an "X" was used to indicate no amino acid could be determined and parentheses were used to delimit amino acids that could not be distinguished. Since Lys-C protease was used to digest the protein, the presence of lysine residues at the N-termini of the peptides was inferred. From the 87 kDa IKKβ band, the sequences of five proteolytic fragments were determined (see FIG. 3, underlined; see, also, Example III).

EXAMPLE II

Identification and Characterization of a Full Length Human IKKα Subunit

This example provides methods for isolating a nucleic acid molecule encoding the IKKα subunit and for characterizing the functional activity of the subunit.

A. Cloning of cDNA Encoding Human IKKα:

Degenerate oligonucleotide (length) sequences of the amino acid sequences of two peptide fragments (SEQ ID NOS: 3 and 4) of the IKKα (see FIG. 1) were searched in the GenBank DNA sequence database. This search revealed that nucleotide sequences encoding both peptide fragments were present in a partial cDNA encoding a portion of a protein designated human CHUK (GenBank Accession #U22512; Connelly and Marcu, supra, 1995).

Based on the human CHUK cDNA sequence, PCR primers were prepared corresponding to the 5'-terminus (5'-CCC<u>CATATG</u>TACCAGCATCGGGAA-3'; SEQ ID NO: 5) and 3'-terminus (3'-CCC<u>CTCGAG</u>TTCTGTTAACCAACT-5';

SEQ ID NO: 6).

SEQ ID NO: 5 also contains a Nde I restriction endonuclease site (underlined) and an ATG (AUG) methionine codon (bold) and SEQ ID NO: 6 also contains an Xho I site. RNA was isolated from HeLa cells and first strand cDNA was prepared and used for a template by PCR using SEQ ID NOS: 5 and 6 as primers. The resulting 2.1 kilobase (kb) fragment was gel purified, $^{32}$P-labeled using oligo-dT and random primers, and used to screen a human fetal brain library (Clontech; Palo Alto Calif.) under high stringency conditions (50% formamide, 42° C.; Sambrook et al., supra, 1989).

In order to obtain the 5'-end of the cDNA encoding IKKα, positive plaques from above were screened by PCR using two internal primers, (5'-CATGGCACCATCGTTCTCTG-3'; SEQ ID NO: 7), which is complementary to the sequence including the Ban I site around position 136 of SEQ ID NO: 1, and (5'-CTCAAAGAGCTCTGGGGCCAGATAC-3'; SEQ ID NO: 8), which is complementary to the sequence including the Sac I site around position 475, and a vector specific primer (TCCGAGATCTGGACGAGC-3'; SEQ ID NO: 9), which is complementary to vector sequences at the 5'-end of the cDNA insert. The longest PCR product was selected and sequenced by the dideoxy method.

DNA sequencing revealed that the cloned IKKα cDNA contained an additional 31 amino acids at the N-terminus as compared to human CHUK. The human IKKα shares a high amount of sequence identity with a protein designated mouse CHUK (GenBank Accession #U12473; Connelly and Marcu, supra, 1995). Although the mouse CHUK contains a domain having characteristics of a serine-threonine protein kinase, no functional activity of the protein was reported and no potential substrates were identified. The putative serine-threonine protein kinase domain of human CHUK was truncated at the N-terminus.

B. Expression of Human IKKα or of an Antisense IKKα Nucleic Acid in a Cell:

The full length IKKα cDNA and a cDNA encoding the Δ31 human CHUK protein (Connelly and Marcu, supra, 1995) were subcloned into the Nde I and Xho I sites of a bacterial expression vector encoding a carboxy terminal FLAG epitope and HIS6 tag. Mammalian cell expression vectors were constructed by cleaving the bacterial expression vector with Nde I and Hind III, to release the cDNA inserts, converting the ends of the inserts to blunt ends using Klenow polymerase, and ligating the cDNA inserts encoding the full length IKKα or the Δ31 human CHUK into pCDNA3 (Invitrogen).

Alternatively, the IKKα cDNA and Δ31 cDNA were subcloned into the Bst XI site of the pRcβactin vector (DiDonato et al., supra, 1996). Orientation of the inserts (sense or antisense) was determined by restriction endonuclease mapping and partial sequence using vector-specific primers. Vector containing the cDNA's inserted in the sense orientation were examined for expression of the encoded product by immunoblot analysis using an antibody specific for the FLAG epitope.

Transfection experiments were performed to determine the effect of expressing the cloned IKKα in HeLa cells or of expressing the cloned IKKα cDNA in the antisense orientation. One day prior to performing the transfections, HeLa cells were split into 35 mm dishes to approximately 50% confluency. Cells were transfected with 0.25 μg of a luciferase reporter gene containing an IL-8 promotor (Eckman et al., *Amer. Soc. Clin. Invest.* 96:1269–1279 (1995), which is incorporated herein by reference) along with either 1 μg pCDNA3 (Invitrogen, La Jolla Calif.; vector control), 1 μg pRcβactin-IKKα-AA (sense orientation), 1 μg pRcβactin-IKKα-K (antisense), or 0.1 μg pCDNA-IKKα-K using the LIPOFECTAMINE method as recommended by the manufacturer (GIBCO/BRL, Gaithersburg Md.). Total DNA concentrations were kept constant by addition of empty pRcβactin DNA.

Transfected cells were incubated in DMEM containing 10% FBS for 24 hr. The cells then were washed and the growth medium was replaced with DMEM containing 0.1% FBS. Cells either were left untreated, or were treated with 20 ng/ml TNFα, 20 ng/ml IL-1α, or 100 ng/ml TPA (phorbol ester) for 3.5 hr. Cells were harvested by scraping and washed once with PBS, then lysed in 100 μl PBS containing 1% TRITON-X100. Luciferase assays were performed using 20 μl of lysate (DiDonato et al., supra, 1995). The protein concentration of each extract was determined using the BIORAD protein assay kit and luciferase activity was normalized according to the protein concentrations.

NF-κB is known to induce expression for the IL-8 promotor. Thus, as expected, treatment of the vector transfected control cells with TNFα, IL-1α or TPA resulted in a 3- to 5-fold increase in normalized luciferase activity. In comparison, in cells transfected with the cDNA encoding IKKα, treatment with TNFα, IL1α or TPA potentiated induction of luciferase activity 5- to 6-fold above the level of induction observed in the vector transfected cells. These results indicate that expression of IKKα in cells increased the amount of NF-κB activated in response to the inducing agents.

In cells transfected with the vector expressing the antisense IKKα nucleic acid molecule, transcription of the luciferase reporter gene induced by IL-1 or TNFα was at the limit of detection, indicating transcription was almost completely inhibited due to expression of the antisense IKKα. This result indicates that the native IKKα is turned over relatively rapidly in the cells. Furthermore, treatment of the cells with the various inducing agents had no effect on the level of luciferase expression of control reporter genes, which are not responsive to NF-κB, as compared to the untreated cells. Other appropriate control experiments were performed in parallel. These results demonstrate the an expression of an antisense IKKα nucleic acid molecule in a cell can specifically inhibit NF-κB mediated gene expression.

EXAMPLE III

Identification and Characterization of a Full Length Human IKKβ Subunit

This example provides methods for isolating a nucleic acid molecule encoding an IKKβ catalytic subunit of IKK and characterizing the activity of the IKKβ subunit.

A. Cloning of IKKβ cDNA:

IKKβ was purified following SDS-PAGE and subjected to internal peptide sequencing (Example I). Five peptide sequences were obtained as follows:

```
KIIDLGYAK (SEQ ID NO:10);

KXVHILN (M/Y) (V/G) (T/N/R/E) (G/N) TI (H/I/S) (SEQ ID NO:11);

KXXIQQD (T/A) GIP (SEQ ID NO:12); KXRVIYTQL (SEQ ID

NO:13); and KXEEVVSLMNEDEK (SEQ ID NO: 20),
``` where amino acid residues that could not be unambiguously determined are indicated by an "X" and where amino acids that could not be distinguished are shown in parentheses. These peptide sequences were used to screen the NCBI EST database and a 336 base pair EST (EST29518; Accession No. AA326115) encoding SEQ ID NOS: 13 and 20 was identified. This EST was determined to correspond to amino acid residues 551 to 661 of SEQ ID NO: 15.

cDNA corresponding to the EST was obtained by PCR using first strand HeLa cDNA as a template and used to probe a human fetal brain library (Clontech). A 1 kb fragment was identified and used as a probe to screen a plasmid based B cell library (Invitrogen). A 3 kb cDNA insert was isolated and sequenced (FIG. 2; SEQ ID NO: 14) and encoded the full length IKKβ (SEQ ID NO: 15), including all five proteolytic fragments (see FIG. 3).

Comparison of the amino acid sequences of IKKα and IKKβ revealed greater than 50% amino acid identity (FIG. 3). In addition, SEQ ID NO: 15 contains a kinase domain, which shares 65% amino acid identity with IKKα, a leucine zipper and a helix-loop-helix domain. Based on the sequence homology and domain structure, the polypeptide (SEQ ID NO: 15) was determined to be a member of the IKK catalytic subunit family of proteins with IKKα and, therefore, was designated IKKβ.

B. Characterization of IKKβ:

This section describes the results of various assays characterizing IKKβ activity, particularly with regard to its association with IKKα. In addition, northern blot analysis revealed that IKKβ and IKKα are coexpressed in most tissues examined, including pancreas, kidney, skeletal muscle, lung, placenta, brain, heart, peripheral blood lymphocytes, colon, small intestine, prostate, thymus and spleen.

1. IKKβ Kinase Activity

The kinase activity associated with IKKβ was characterized using HeLa or 293 cells transiently transfected with an HA-tagged IKKβ expression vector. Transfected cells were stimulated with 20 ng/ml TNF for 10 min and HA-IKKβ was isolated by immunoprecipitation using anti-HA antibody (Kolodziej and Young, *Meth. Enzymol.* 194:508–519 (1991)). The immune complexes were tested for the ability to phosphorylate wild type (wt) and mutant forms of IκBα and IκBβ (see Example I).

Similarly to the purified IKK complex and the complex associated with IKKα, the IKKβ immune complex phosphorylated wt IκBα and IκBβ, but not mutants in which the inducible phosphorylation sites (Ser-32 and Ser-36 for IκBα and Ser-19 and Ser-23 for IκBα) were replaced with either alanines or threonines. However, a low level of residual phosphorylation of full length IκBα(A32/A36) was observed due to phosphorylation of sites in the C-terminal portion of the protein (DiDonato et al., supra, 1997). Single substitution mutants, IκBα(A32) and IκB(A36), were phosphorylated almost as efficiently as wt IκBα, indicating that IKKβ-associated IKK activity can phosphorylate IκBα at both Ser-32 and Ser-36.

The response of IKKβ-associated kinase activity to various stimuli also was examined in HeLa cells transiently transfected with the HA-IKKβ expression vector. After 24 hr, the cells were stimulated with either 10 ng/ml IL-1, 20 ng/ml TNF or 100 ng/ml TPA, then HA-IKKβ immune complexes were isolated by immunoprecipitation and IKK activity was measured. TNF and IL-1 potently stimulated IKKβ-associated kinase activity, whereas the response to TPA was weaker. The kinetics of IKKβ activation by either TNF or IL-1 essentially were identical to the kinetics of activation of the IKKα-associated IκB kinase measured by a similar protocol.

2. Functional Interactions Between IKKα and IKKβ

As shown in Example I, IKKα and IKKβ copurified in about a 1:1 ratio through several chromatographic steps, suggesting that the two proteins interact with each other. The ability of the IKK subunits to interact in a functional complex and the effect of each subunit on the activity of the other subunit was examined using 293 cells transfected with expression vectors encoding Flag(M2)-IKKα or M2-IKKα and HA-IKKα, either alone or in combination (see Hopp et al., *BioTechnology* 6:1204–1210 (1988)). After 24 hr, samples of the cells were stimulated with TNF, lysates were prepared from stimulated and unstimulated cells, and one portion of the lysates was precipitated with anti-Flag antibodies (Eastman Kodak Co.; New Haven Conn.) and another portion was precipitated with anti-HA antibodies. The IKK activity associated with the different immune complexes and their content of IKKα and IKKβ were measured.

Considerably more basal IKK activity was precipitated with HA-IKKβ than with Flag-IKKα. However, the activity associated with HA-IKKβ was further elevated upon coexpression of M2-IKKα and the low basal activity associated with Flag-IKKα was strongly augmented by coexpression of IKKβ. Immunoblot analysis revealed that the potentiating effect of such coexpression was not due to changes in the level of expression of IKKα or IKKβ.

The levels of IKK activities associated with IKKα and IKKβ were compared more precisely by transfecting 293 cells with increasing amounts of HA-IKKα or HA-IKKβ expression vectors (0.1 to 0.5 $\mu$g/$10^6$ cells) and determining the kinase activities associated with the two proteins in cell lysates prepared before or after TNF stimulation (20 ng/ml, 5 min); GST-IκBα(1–54) was used as substrate. The level of expression of each protein was determined by immunoblot analysis and used to calculate the relative levels of specific IKK activity.

The HA-IKKα-associated IKK had a low level of basal specific activity, whereas expression of HA-IKKβ resulted in high basal specific activity that was increased when higher amounts of HA-IKKβ were expressed. However, the specific IKK activity associated with either IKKα or IKKβ isolated from TNF-stimulated cells was very similar and was not considerably affected by their expression level. These results indicate that titration of a negative regulator or formation of a constitutively active IKK complex can occur due to overexpression of IKKβ.

The ability of IKKα and IKKβ to physically interact was examined. Immunoblot analysis demonstrated that precipitation of HA-IKKβ using an anti-HA antibody coprecipitated both endogenous IKKα and coexpressed Flag-IKKα, as indicated by the higher amount of coprecipitating IKKα detected after cotransfection with Flag-IKKα. Similarly, immunoprecipitation of Flag-IKKα with anti-Flag(M2) antibody resulted in coprecipitation of cotransfected HA-IKKβ. Exposure of the cells to TNF had no significant effect on the association of IKKα and IKKβ.

The interaction between IKKα and IKKβ was further examined by transfecting HeLa cells with various amounts (0.1 to 1.0 $\mu$g/$10^6$ cells) of the HA-IKKβ vector. After 24 hr, the cells were incubated for 5 min in the absence or presence of 20 ng/ml TNF, then lysed. The lysates were examined for IKK activity and for the amount of HA-IKKβ and endogenous IKKα. Expression of increasing amounts of HA-IKKβ resulted in higher basal levels of IKK activity and increasing amounts of coprecipitated IKKα. The level of TNF stimulated IKK activity increased only marginally in response to IKKβ overexpression and TNF had no effect on the association of IKKβ and IKKα.

Since the results described above revealed that HA-IKKβ associates with endogenous IKKα to generate a functional cytokine-regulated IKK complex, this association was examined further by transfecting HeLa cells with either empty expression vector or small amounts (1 $\mu$g/60 mm plate) of either HA-IKKα or HA-IKKβ vectors. After 24 hr, samples of the transfected cell populations were stimulated with 20 ng/ml TNF for 5 min, then cell lysates were prepared and separated by gel filtration on a SUPEROSE 6 column. One portion of each column fraction was immunoprecipitated with a polyclonal antibody specific for IKKα and assayed for IKKα-associated IKK activity, while a second portion was precipitated with anti-HA antibody and examined for HA-IKKβ- or HA-IKKα-associated IKK activity. Relative specific activity was determined by immunoprecipitating the complexes, separating the proteins by SDS-PAGE, blotting the proteins onto IMOBILON membranes (Millipore; Bedford Mass.), immunoblotting with anti-HA antibody and quantitating the levels of IκB phosphorylation and HA-tagged proteins by phosphoimaging. The results demonstrated that endogenous IKKα-associated IKK activity exists as two complexes, a larger complex of approximately 900 kDa and a smaller one of approximately 300 kDa. Stimulation with TNF increased the IKK activity of both complexes, although the extent of increase was considerably greater for the 900 kDa complex.

HA-IKKβ-associated IKK activity had exactly the same distribution as the IKKα-associated activity, eluting at 900 kDa and 300 kDa and, again, the extent of TNF responsiveness was considerably greater for the 900 kDa complex. Comparison to the IKKα-associated activity in cells transfected with the empty vector indicated that HA-IKKβ expression produced a modest, approximately 2-fold increase in the relative amount of IKK activity associated with the smaller 300 kDa complex. These results indicate that the 300 kDa IKK complex, like the 900 kDa complex, contains both IKKα and IKKβ. However, the 300 kDa lacks other subunits present in the 900 kDa complex. When IKKβ was overexpressed, the relative amount of the smaller complex increased, indicating that some of the subunits that are unique to the larger complex are present in a limited amount.

3. Both IKKα and IKKβ Contribute to IKK Activity

The relative contribution of IKKα and IKkβ to IKK activity was examined by constructing mutant subunits in which the lysine (K) codon present at position 44 of each subunit was substituted with a codon for either methionine (M) or alanine (A) codon, respectively. Similar mutations in other protein kinases render the enzymes defective in binding ATP and, therefore, catalytically inactive (Taylor et al., *Ann. Rev. Cell Biol.* 8:429–462 (1992)). The activity of the IKK mutants was compared to the activity of their wild type (wt) counterparts by cell-free translation in reticulocyte lysates using GST-IκBα (1–54) as a substrate. Translation of IKKα (KM) resulted in formation of IκB kinase having only slightly less activity than the IKK formed by translation of wt IKKα. In comparison, translation of IKKβ (KA) did not generate IKK activity. Translation of wt IKKβ generated IκB kinase activity as expected.

The activities of the different proteins also was examined by transient transfection in mammalian cells. Expression and immunoprecipitation of HA-IKKα (KM) resulted in isolation of cytokine stimulated IKK activity that, after TNF stimulation, was 2-to 3-fold lower than the activity of IKK formed by wt HA-IKKα isolated from TNF-stimulated cells. Similarly, expression and immunoprecipitation of HA-IKKβ resulted in formation of a cytokine responsive IKK activity that, after TNF stimulation, was 3- to 5-fold lower than the activity of IKK generated by wt HA-IKKβ isolated from TNF stimulated cells. In contrast to results obtained by overexpression of wt HA-IKKβ, however, overexpression of HA-IKKα (KA) did not result in the generation of basal IKK activity. Immunoprecipitation experiments revealed that IKKα (KM) associates IKKβ and that IKKβ (KA) associates with IKKα and that both IKKα and IKKβ undergo homotypic interactions as efficiently as they undergo heterotypic interactions.

Autophosphorylation of wt and kinase-defective HA-IKKα and HA-IKKβ was examined in transiently transfected HeLa cells. HeLa cells expressing these proteins were treated with TNF for 10 min, then cell lysates of TNF treated or untreated cells were immunoprecipitated with HA antibodies and the immune complexes were subjected to a phosphorylation reaction (DiDonato et al., supra, 1997). Both wt HA-IKKα and wt HA-IKKβ were phosphorylated and their autophosphorylation was enhanced in TNF-stimulated extracts. In contrast, the kinase-defective IKKα or IKKβ mutants did not exhibit significant autophosphorylation.

4. The Role of the LZ and HLH Motifs in IKKα and IKKβ

IKKα and IKKβ both contain leucine zipper (LZ) and helix-loop-helix (HLH) motifs, which are known to mediate protein—protein interactions through their hydrophobic surfaces. The role of the LZ motif in the IKK subunit interaction was examined using an IKKα mutant in which the L462 and L469 residues within the LZ region were substituted with serine residues. The role of the HLH motif was examined using an HLH mutant of IKKα containing a substitution of L605 with arginine (R) and of F606 with proline (P). The activity of the IKKα LZ$^-$ and HLH$^-$ mutants was examined by transient transfection in 293 cells, either alone or in the presence of cotransfected Flag-IKKα.

Expression of wt HA-IKKα generated substantial IKK activity that was isolated by immunoprecipitation with anti-HA, whereas very little IKK activity was generated in cells transfected with either the HA-IKKα (LZ)$^-$ or HA-IKKα (HLH)$^-$ mutant. Coexpression of the mutant IKK subunits with Flag-IKKβ resulted in a substantial increase in the IKK activity isolated by immunoprecipitation of HA-IKKβ, but had no effect on the very low activity that coprecipitated with HA-IKKα (LZ)$^-$. However, coexpression of Flag-IKKβ did stimulate the low level of IKK activity associated with HA-IKKα (HLH)$^-$. Probing of the HA immune complexes with anti-Flag(M2) antibodies indicated that both wt HA-IKKα and HA-IKKα (HLH)$^-$ associated with similar amounts of Flag-IKKβ, but that the HA-IKKα (LZ) mutant did not associate with Flag-IKKβ. These results indicate that the lower IκB kinase activity associated with the IKKα (LZ)$^-$ mutant is due to a defect in its ability to interact with IKKβ. The lower IκB kinase activity of the IKKα (HLH)$^-$ mutant, on the other hand, likely is due to a defect in the ability to interact with a second, undefined protein, since the HLH mutant can interact with IKKβ.

5. Both IKKα and IKKβ are Necessary for NF-κB Activation

The contribution of IKKα and IKKβ to NF-κB activation was examined using HeLa cells transfected with expression vectors encoding HA-tagged wt IKKα, IKKα (KM), wt IKKβ and IKKβ (KA); an HA-JNK1 vector was used as a control. NF-κB activation was assessed by examining the subcellular distribution of RelA(p65) by indirect immunofluorescence.

HeLa cells were grown on glass cover slips in growth medium, then transfected with 1 μg plasmid DNA by the lipofectamine method. After 24 hr, samples of cells were stimulated with 20 ng/ml TNF for 30 min, then stimulated or unstimulated cells were washed with PBS and fixed with 3.5% formaldehyde in PBS for 15 min at room temperature (RT). The fixed cells were permeablized with 0.02% NP-40 in PBS for 1 min, then incubated with 100% goat serum at 4° C. for 12 hr. The cells then were washed 3 times with PBS and incubated with a mixture of a rabbit anti-NF-κB p65 (RelA) antibody (1:100 dilution; Santa Cruz Biotech) and a mouse monoclonal anti-HA antibody in PBS containing 1% BSA and 0.2% TRITON X-100 at 37° C. for 2 hr. Cells then were washed 3 times with PBS containing 0.2% TRITON X-100 and incubated for 2 hr at RT with secondary antibodies, fluorescein-conjugated goat affinity purified anti-mouse IgG-IgM and rhodamine-conjugated IgG fraction goat anti-rabbit IgG (1:200 dilution; Cappel). Cells were washed 4 times with PBS containing 0.2% TRITON X-100, then covered with a drop of gelvatol mounting solution and viewed and photographed using a Zeiss Axioplan microscope equipped for epifluorescence with the aid of fluorescein and rhodamine specific filters.

Double staining with both anti-RelA and anti-HA revealed that expression of moderate amounts of either wt IKKα or wt IKKβ did not produce considerable stimulation of RelA nuclear translocation. In addition, the wt IKK proteins did not interfere with the nuclear translocation of RelA induced by TNF treatment. However, expression of similar levels of either IKKα (KM) or IKKβ (KA), as determined by the intensity of the fluorescent signal, inhibited the nuclear translocation of RelA in TNF-treated cells. Expression of HA-JNK1 had no effect on the subcellular distribution of RelA. Since the subcellular distribution of RelA is dependent on the state and abundance of IκB, these results indicate that expression of either IKKα (KM) or IKKβ (KA) inhibits the induction of IκB phosphorylation and degradation by TNF.

EXAMPLE IV

Isolation of IκB Kinase Complex

This example demonstrates a method for isolating the 900 kDa IκB kinase complex comprising an IKKα polypeptide.

Proteins that associate with IKKα in vivo were isolated by immunoprecipitation using HIS6 and FLAG epitope tags. The HIS6-FLAG-IKKα (HF-IKKα) encoding construct was prepared using a double stranded oligonucleotide,

5'-AGCTTGCGCGTATGGCTTCGGGTCATCACCATCACCA (SEQ ID NO: 16),

TCACGGTGACTACAAGGACGACGATGACAAAGGTGACATCGAAGGTAGAGGTCA-3' which encodes six histidine residues (HIS6), the FLAG epitope and the factor Xa site in tandem. The oligonucleotide was inserted using HindIII-NdeI site in frame with the N-terminus of the IKKα coding sequence in the BLUESCRIPT KS plasmid (Stratagene; La Jolla Calif.). The HindIII-NotI fragment of this plasmid, which contains the HF-IKKα cDNA sequence, was subcloned into the pRcβactin mammalian expression vector, which contains a nucleic acid sequence conferring neomycin resistance, to produce plasmid pRC-HF-IKKα. Expression of the HF-IKKα polypeptide was confirmed by western blot analysis using anti-FLAG antibodies.

pRC-HF-IKKα was transfected into human embryonic kidney 293 cells and transfected cells were selected for growth in the presence of G418. A low basal level of IKK activity was detected in cells expressing HF-IKKα and IKK activity increased several fold when the cells were treated with TNFα. This result indicates that the HF-IKKα expression in 293 cells is associated with IKK activity in the cells and that such IKK activity is inducible in response to TNFα.

A 293 cell line that expresses HF-IKKα was selected and expanded to approximately $4 \times 10^8$ cells. The cells were treated with 10 ng/ml TNFα for 5 min, then harvested in ice cold PBS by centrifugation at 2500×g. The cell pellet was washed with ice cold PBS, resuspended in lysis buffer (20 mM Tris, pH 7.6), 150 mM NaCl, 1% TRITON X-100, 20 mM β-glycerophosphate, 2 mM PNPP, 1 mM $Na_3VO_4$, 5 mM β-mercaptoethanol, 1 mM EDTA, 0.5 mM EGTA, 1 mM PMSF, 3 μg/ml pepstatin, 3 μg/ml leupeptin, 10 μg/ml bestatin and 25 μg/ml aprotinin), and lysed by 20 strokes in a glass Dounce homogenizer (pestle A).

The homogenate was centrifuged at 15,000 rpm in a Beckman SS34 rotor for 30 min at 40° C. The supernatant was collected, supplemented with 20 mM imidazole and 300 mM NaCl, then mixed with 0.5 ml of a 50% slurry of Ni-NTA (nickel nitrilotriacetic acid; Qiagen, Inc.; Chatsworth Calif.) and stirred for 4 hr at 4° C. Following incubation, the resin was pelleted at 200×g and the supernatant was removed. The resin was washed 3 times with 50 ml binding buffer containing 25 mM imidazole.

Proteins bound to the resin were eluted in 2 ml binding buffer containing 150 mM imidazole and 20 mM DTT. The eluate was mixed with 100 μl of a 50% slurry of anti-FLAG antibody coupled to SEPHAROSE resin using the AMINOLINK PLUS immobilization kit (Pierce Chem. Co.; Rockford Ill.) and stirred for 4 hr at 4° C. The resin was pelleted at 1000×g, the supernatant was removed, and the resin was washed with 10 ml binding buffer (without imidazole). Proteins bound to the resin then were eluted with 1% SDS or with FLAG peptide and examined by 10% SDS-PAGE Silver staining revealed the presence of seven proteins, including the HF-IKKα, which was confirmed by western blot analysis using anti-FLAG antibody. The copurified proteins had apparent molecular masses of about 100 kDa, 63 kDa, 60 kDa, 55 kDa, 46 kDa and 29 kDa; the endogenous 87 kDa IKKβ comigrates with the HA-IKKα protein. These results indicate that IKKα, along with some or all of the copurifying proteins, comprise the 900 kDa IκB kinase complex.

EXAMPLE V

Anti-IKK Antisera

This example provides a method of producing anti-IKK antisera.

Anti-IKKα antibodies were raised in rabbits using either His-tagged IKKα expressed in *E. coli* or the IKKα peptide ERPPGLRPGAGGPWE (SEQ ID NO: 17) or

TIIHEAWEEQGNS (SEQ ID NO: 18)

as an immunogen. Anti-IKKβ antibodies were raised using the peptide SKVRGPVSGSPDS (SEQ ID NO: 19). The peptides were conjugated to keyhole limpet hemocyanin (Sigma Chemical Co.; St. Louis Mo.). Rabbits were immunized with 250 to 500 μg conjugated peptide in complete Freund's adjuvant. Three weeks after the primary immunization, booster immunizations were performed using 50 to 100 μg immunogen and were repeated three times, at 3 to 4 week intervals. Rabbits were bled one week after the final booster and antisera were collected. Anti-IKKα antiserum was specific for IKKα and did not cross react with IKKβ.

EXAMPLE VI

Use of an IKK Subunit In A Drug Screening Assay

This example describes an assay for screening for agents such as drugs that alter the association of an IKK subunit and a second protein that specifically associates with the IKK subunit.

A GST-IKK subunit fusion protein or HIS6-IKK subunit fusion protein can be prepared using methods as described above and purified using glutathione- or metal-chelation chromatography, respectively (Smith and Johnson, *Gene* 67:31–40 (1988), which is incorporated herein by reference; see, also, Example IV). The fusion protein is immobilized to a solid support taking advantage of the ability of the GST protein to specifically bind glutathione or of the HIS6 peptide region to chelate a metal ion such as nickel (Ni) ion or cobalt (Co) ion (Clontech) by immobilized metal affinity chromatography. Alternatively, an anti-IKK antibody can be immobilized on a matrix and the IKK-α can be allowed to bind to the antibody.

The second protein, which can be IκB or a protein that copurifies with IKK subunit as part of the 900 kDa IκB kinase, for example, can be detectably labeled with a moiety such as a fluorescent molecule or a radiolabel (Hermanson, supra, 1996), then contacted in solution with the immobilized IKK subunit under conditions as described in Example I, which allow IκB to specifically associate with the IKK subunit. Preferably, the reactions are performed in 96 well plates, which allow automated reading of the reactions. Various agents such as drugs then are screened for the ability to alter the association of the IKK subunit and IκB.

The agent and labeled IκB, for example, can be added together to the immobilized IKK subunit, incubated to allow binding, then washed to remove unbound labeled IκB. The relative amount of binding of labeled IκB in the absence as compared to the presence of the agent being screened is determined by detecting the amount of label remaining in the plate. Appropriate controls are performed to account, for example, for nonspecific binding of the labeled IκB to the matrix. Such a method allows the identification of an agent that alter the association of an IKK subunit and a second protein such as IκB.

Alternatively, the labeled IκB or other appropriate second protein can be added to the immobilized IKK subunit and allowed to associate, then the agent can be added. Such a method allows the identification of agents that can induce the dissociation of a bound complex comprising the IKK subunit and IκB. Similarly, a screening assay of the invention can be performed using the 900 kDa IKK complex, comprising an IKK subunit.

Although the invention has been described with reference to the examples provided above, it should be understood that various modifications can be made without departing from the spirit of the invention. Accordingly, the invention is limited only by the claims.

We claim:

1. An isolated human IκB kinase (IKK) subunit, IKKβ, wherein said IKKβ phosphorylates serine-32 and serine-36 of IκBα and has an apparent molecular mass of 87 kiloDaltons as determined by SDS-polyacrylamide gel electrophoresis in an 8% gel under reducing conditions.

2. The isolated IKKβ of claim 1, comprising an amino acid sequence as shown in SEQ ID NO: 15.

3. The isolated IKKβ of claim 1, wherein said isolated IKKβ comprises one or more sequences selected from the group consisting of SEQ ID NO:11, SEQ ID NO:12, SEQ ID NO:13, and SEQ ID NO:20.

4. The isolated IKKβ of claim 3, wherein said isolated IKKβ comprises two or more sequences selected from the group consisting of SEQ ID NO:10, SEQ ID NO:11, SEQ ID NO:12, SEQ ID NO:13, and SEQ ID NO:20.

5. The isolated IKKβ of claim 4, wherein said isolated IKKβ comprises three or more sequences selected from the group consisting of SEQ ID NO:10, SEQ ID NO:11, SEQ ID NO:12, SEQ ID NO:13, and SEQ ID NO:20.

6. The isolated IKKβ of claim 5, wherein said isolated IKKβ comprises four or more sequences selected from the group consisting of SEQ ID NO:10, SEQ ID NO:11, SEQ ID NO:12, SEQ ID NO:13, and SEQ ID NO:20.

7. The isolated IKKβ of claim 1, wherein said isolated IKKβ comprises SEQ ID NO:10, SEQ ID NO:11, SEQ ID NO:12, SEQ ID NO:13, and SEQ ID NO:20.

8. The isolated IKKβ of claim 1, wherein said isolated IKKβ comprises amino acid 36 to amino acid 300 of SEQ ID NO:15.

9. The isolated IKKβ of claim 1, wherein said isolated IKKβ comprises amino acid 603 to amino acid 642 of SEQ ID NO:15.

10. The isolated IKKβ of claim 1, wherein said isolated IKKβ comprises amino acid 458 to amino acid 486 of SEQ ID NO:15.

11. The isolated IKKβ of claim 1, wherein said isolated IKKβ comprises two or more sequences selected from the group consisting of amino acid 36 to amino acid 300 of SEQ ID NO:15, amino acid 603 to amino acid 642 of SEQ ID NO:15, and amino acid 458 to amino acid 486 of SEQ ID NO:15.

12. The isolated IKKβ of claim 1, wherein said isolated IKKβ comprises amino acid 36 to amino acid 300 of SEQ ID NO:15, amino acid 603 to amino acid 642 of SEQ ID NO:15, and amino acid 458 to amino acid 486 of SEQ ID NO:15.

13. A method of identifying an agent that modulates the specific association of an IKKβ and IKB protein, comprising the steps of:

a) providing:
 the isolated IKKβ of claim 1;
 ii) IκB protein; and
 iii) said agent;

b) contacting said isolated IKKβ, said IκB protein, and said agent under conditions suitable for the specific association of said IKKβ and said IκB protein; and c) detecting an altered association of said IKKβ and said IκB protein in the presence of said agent, wherein said altered association identifies said agent as modulating the specific association of said IKKβ and said IκB protein.

14. The method of claim 13, wherein said IκB protein is chosen from one or more of IκBβ and IκBβ.

15. A method of identifying an agent that modulates the specific association of an IKKβ and a protein chosen from one or more of IKBβ and IKBβ, comprising the steps of:

a) providing:
 i) the isolated IKKβ of claim 10;
 ii) said protein; and
 iii) said agent;

b) contacting said isolated IKKβ, said proteing, and said agent under conditions suitable for the specific association of said IKKβ and said protein; and c) detecting an altered association of said IKKβ and said protein in the presence of said agent, wherein said altered association identifies said agent as modulating the specific association of said IKKβ and said protein.

16. The method of claim 13, wherein said agent is a mutant IκB protein chosen from one or more of (1) mutant IκBβ containing amino acid substitutions for serine-32 and for serine-36, and (2) mutant IκBβ containing amino acid substitutions for serine-19 and for serine-23.

17. The method of claim 13, wherein said isolated IKKβ comprises SEQ ID NO:15.

18. A method for identifying an agent that alters IKKβ activity, comprising the steps of:
  a) providing:
     i) the isolated IKKβ of claim 1; and
     ii) said agent;
  b) incubating said isolated IKKβ with said agent; and
  c) determining altered IκB kinase activity of said isolated IKKβ in the presence of said agent, wherein said altered IκB activity identifies said agent as altering IKKβ activity.

19. The method of claim 18, wherein said isolated IKKβ comprises a 300 kDa IκB kinase complex or a 900 kDa IκB kinase complex.

20. The method of claim 18, wherein said isolated IKKβ comprises SEQ ID NO:15.

* * * * *

UNITED STATES PATENT AND TRADEMARK OFFICE
CERTIFICATE OF CORRECTION

PATENT NO. : 6,689,575 B2
DATED : February 10, 2004
INVENTOR(S) : Karin et al.

Page 1 of 1

It is certified that error appears in the above-identified patent and that said Letters Patent is hereby corrected as shown below:

Column 66,
Line 29, please delete "and IKB protein" and insert -- and IκB protein --.
Line 45, please delete "more of IκBβ" and insert -- more of IκBα --.
Line 48, please delete "IKBβ and IKBβ" and insert -- IκBα and IκBβ --.
Line 50, please delete "of claim 10" and insert -- of claim 1 --.
Line 63, please delete "IκBβ containing" and insert -- IκBα containing --.

Signed and Sealed this

Twenty-seventh Day of April, 2004

JON W. DUDAS
*Acting Director of the United States Patent and Trademark Office*

SEQUENCE LISTING

```
<160> NUMBER OF SEQ ID NOS: 20

<210> SEQ ID NO 1
<211> LENGTH: 2273
<212> TYPE: DNA
<213> ORGANISM: Homo sapiens
<220> FEATURE:
<221> NAME/KEY: CDS
<222> LOCATION: (36)..(2273)

<400> SEQUENCE: 1
tcgacggaac ctgaggccgc ttgccctccc gcccc atg gag cgg ccc ccg ggg        53
                                       Met Glu Arg Pro Pro Gly
                                       1               5 ctg cgg ccg ggc gcg ggc ggg ccc tgg gag atg cgg gag cgg ctg ggc      101
Leu Arg Pro Gly Ala Gly Gly Pro Trp Glu Met Arg Glu Arg Leu Gly
            10                  15                  20 acc ggc ggc ttc ggg aac gtc tgt ctg tac cag cat cgg gaa ctt gat      149
Thr Gly Gly Phe Gly Asn Val Cys Leu Tyr Gln His Arg Glu Leu Asp
        25                  30                  35 ctc aaa ata gca att aag tct tgt cgc cta gag cta agt acc aaa aac      197
Leu Lys Ile Ala Ile Lys Ser Cys Arg Leu Glu Leu Ser Thr Lys Asn
    40                  45                  50 aga gaa cga tgg tgc cat gaa atc cag att atg aag aag ttg aac cat      245
Arg Glu Arg Trp Cys His Glu Ile Gln Ile Met Lys Lys Leu Asn His
55                  60                  65                  70 gcc aat gtt gta aag gcc tgt gat gtt cct gaa gaa ttg aat att ttg      293
Ala Asn Val Val Lys Ala Cys Asp Val Pro Glu Glu Leu Asn Ile Leu
                75                  80                  85 att cat gat gtg cct ctt cta gca atg gaa tac tgt tct gga gga gat      341
Ile His Asp Val Pro Leu Leu Ala Met Glu Tyr Cys Ser Gly Gly Asp
            90                  95                  100 ctc cga aag ctg ctc aac aaa cca gaa aat tgt tgt gga ctt aaa gaa      389
Leu Arg Lys Leu Leu Asn Lys Pro Glu Asn Cys Cys Gly Leu Lys Glu
        105                 110                 115 agc cag ata ctt tct tta cta agt gat ata ggg tct ggg att cga tat      437
Ser Gln Ile Leu Ser Leu Leu Ser Asp Ile Gly Ser Gly Ile Arg Tyr
    120                 125                 130 ttg cat gaa aac aaa att ata cat cga gat cta aaa cct gaa aac ata      485
Leu His Glu Asn Lys Ile Ile His Arg Asp Leu Lys Pro Glu Asn Ile
135                 140                 145                 150 gtt ctt cag gat gtt ggt gga aag ata ata cat aaa ata att gat ctg      533
Val Leu Gln Asp Val Gly Gly Lys Ile Ile His Lys Ile Ile Asp Leu
                155                 160                 165 gga tat gcc aaa gat gtt gat caa gga agt ctg tgt aca tct ttt gtg      581
Gly Tyr Ala Lys Asp Val Asp Gln Gly Ser Leu Cys Thr Ser Phe Val
            170                 175                 180 gga aca ctg cag tat ctg gcc cca gag ctc ttt gag aat aag cct tac      629
Gly Thr Leu Gln Tyr Leu Ala Pro Glu Leu Phe Glu Asn Lys Pro Tyr
        185                 190                 195 aca gcc act gtt gat tat tgg agc ttt ggg acc atg gta ttt gaa tgt      677
Thr Ala Thr Val Asp Tyr Trp Ser Phe Gly Thr Met Val Phe Glu Cys
```

```
                                                        -continued

Thr Ala Thr Val Asp Tyr Trp Ser Phe Gly Thr Met Val Phe Glu Cys
    200                 205                 210 att gct gga tat agg cct ttt ttg cat cat ctg cag cca ttt acc tgg    725
Ile Ala Gly Tyr Arg Pro Phe Leu His His Leu Gln Pro Phe Thr Trp
215                 220                 225                 230 cat gag aag att aag aag aag gat cca aag tgt ata ttt gca tgt gaa    773
His Glu Lys Ile Lys Lys Lys Asp Pro Lys Cys Ile Phe Ala Cys Glu
                    235                 240                 245 gag atg tca gga gaa gtt cgg ttt agt agc cat tta cct caa cca aat    821
Glu Met Ser Gly Glu Val Arg Phe Ser Ser His Leu Pro Gln Pro Asn
                250                 255                 260 agc ctt tgt agt tta ata gta gaa ccc atg gaa aac tgg cta cag ttg    869
Ser Leu Cys Ser Leu Ile Val Glu Pro Met Glu Asn Trp Leu Gln Leu
            265                 270                 275 atg ttg aat tgg gac cct cag cag aga gga gga cct gtt gac ctt act    917
Met Leu Asn Trp Asp Pro Gln Gln Arg Gly Gly Pro Val Asp Leu Thr
280                 285                 290 ttg aag cag cca aga tgt ttt gta tta atg gat cac att ttg aat ttg    965
Leu Lys Gln Pro Arg Cys Phe Val Leu Met Asp His Ile Leu Asn Leu
295                 300                 305                 310 aag ata gta cac atc cta aat atg act tct gca aag ata att tct ttt   1013
Lys Ile Val His Ile Leu Asn Met Thr Ser Ala Lys Ile Ile Ser Phe
                    315                 320                 325 ctg tta cca cct gat gaa agt ctt cat tca cta cag tct cgt att gag   1061
Leu Leu Pro Pro Asp Glu Ser Leu His Ser Leu Gln Ser Arg Ile Glu
                330                 335                 340 cgt gaa act gga ata aat act ggt tct caa gaa ctt ctt tca gag aca   1109
Arg Glu Thr Gly Ile Asn Thr Gly Ser Gln Glu Leu Leu Ser Glu Thr
            345                 350                 355 gga att tct ctg gat cct cgg aaa cca gcc tct caa tgt gtt cta gat   1157
Gly Ile Ser Leu Asp Pro Arg Lys Pro Ala Ser Gln Cys Val Leu Asp
360                 365                 370 gga gtt aga ggc tgt gat agc tat atg gtt tat ttg ttt gat aaa agt   1205
Gly Val Arg Gly Cys Asp Ser Tyr Met Val Tyr Leu Phe Asp Lys Ser
375                 380                 385                 390 aaa act gta tat gaa ggg cca ttt gct tcc aga agt tta tct gat tgt   1253
Lys Thr Val Tyr Glu Gly Pro Phe Ala Ser Arg Ser Leu Ser Asp Cys
                    395                 400                 405 gta aat tat att gta cag gac agc aaa ata cag ctt cca att ata cag   1301
Val Asn Tyr Ile Val Gln Asp Ser Lys Ile Gln Leu Pro Ile Ile Gln
                410                 415                 420 ctg cgt aaa gtg tgg gct gaa gca gtg cac tat gtg tct gga cta aaa   1349
Leu Arg Lys Val Trp Ala Glu Ala Val His Tyr Val Ser Gly Leu Lys
            425                 430                 435 gaa gac tat agc agg ctc ttt cag gga caa agg gca gca atg tta agt   1397
Glu Asp Tyr Ser Arg Leu Phe Gln Gly Gln Arg Ala Ala Met Leu Ser
440                 445                 450 ctt ctt aga tat aat gct aac tta aca aaa atg aag aac act ttg atc   1445
Leu Leu Arg Tyr Asn Ala Asn Leu Thr Lys Met Lys Asn Thr Leu Ile
455                 460                 465                 470 tca gca tca caa caa ctg aaa gct aaa ttg gag ttt ttt cac aaa agc   1493
Ser Ala Ser Gln Gln Leu Lys Ala Lys Leu Glu Phe Phe His Lys Ser
                    475                 480                 485 att cag ctt gac ttg gag aga tac agc gag cag atg acg tat ggg ata   1541
Ile Gln Leu Asp Leu Glu Arg Tyr Ser Glu Gln Met Thr Tyr Gly Ile
                490                 495                 500 tct tca gaa aaa atg cta aaa gca tgg aaa gaa atg gaa gaa aag gcc   1589
Ser Ser Glu Lys Met Leu Lys Ala Trp Lys Glu Met Glu Glu Lys Ala
            505                 510                 515
```

-continued

| | |
|---|---|
| atc cac tat gct gag gtt ggt gtc att gga tac ctg gag gat cag att<br>Ile His Tyr Ala Glu Val Gly Val Ile Gly Tyr Leu Glu Asp Gln Ile<br>520                         525                    530 | 1637 |
| atg tct ttg cat gct gaa atc atg gag cta cag aag agc ccc tat gga<br>Met Ser Leu His Ala Glu Ile Met Glu Leu Gln Lys Ser Pro Tyr Gly<br>535                      540                    545                550 | 1685 |
| aga cgt cag gga gac ttg atg gaa tct ctg gaa cag cgt gcc att gat<br>Arg Arg Gln Gly Asp Leu Met Glu Ser Leu Glu Gln Arg Ala Ile Asp<br>                555                    560                    565 | 1733 |
| cta tat aag cag tta aaa cac aga cct tca gat cac tcc tac agt gac<br>Leu Tyr Lys Gln Leu Lys His Arg Pro Ser Asp His Ser Tyr Ser Asp<br>570                        575                    580 | 1781 |
| agc aca gag atg gtg aaa atc att gtg cac act gtg cag agt cag gac<br>Ser Thr Glu Met Val Lys Ile Ile Val His Thr Val Gln Ser Gln Asp<br>585                      590                    595 | 1829 |
| cgt gtg ctc aag gag cgt ttt ggt cat ttg agc aag ttg ttg ggc tgt<br>Arg Val Leu Lys Glu Arg Phe Gly His Leu Ser Lys Leu Leu Gly Cys<br>600                        605                    610 | 1877 |
| aag cag aag att att gat cta ctc cct aag gtg gaa gtg gcc ctc agt<br>Lys Gln Lys Ile Ile Asp Leu Leu Pro Lys Val Glu Val Ala Leu Ser<br>615                      620                    625                630 | 1925 |
| aat atc aaa gaa gct gac aat act gtc atg ttc atg cag gga aaa agg<br>Asn Ile Lys Glu Ala Asp Asn Thr Val Met Phe Met Gln Gly Lys Arg<br>                635                    640                    645 | 1973 |
| cag aaa gaa ata tgg cat ctc ctt aaa att gcc tgt aca cag agt tct<br>Gln Lys Glu Ile Trp His Leu Leu Lys Ile Ala Cys Thr Gln Ser Ser<br>650                        655                    660 | 2021 |
| gcc cgc tct ctt gta gga tcc agt cta gaa ggt gca gta acc cct caa<br>Ala Arg Ser Leu Val Gly Ser Ser Leu Glu Gly Ala Val Thr Pro Gln<br>665                      670                    675 | 2069 |
| gca tac gca tgg ctg gcc ccc gac tta gca gaa cat gat cat tct ctg<br>Ala Tyr Ala Trp Leu Ala Pro Asp Leu Ala Glu His Asp His Ser Leu<br>680                        685                    690 | 2117 |
| tca tgt gtg gta act cct caa gat ggg gag act tca gca caa atg ata<br>Ser Cys Val Val Thr Pro Gln Asp Gly Glu Thr Ser Ala Gln Met Ile<br>695                      700                    705                710 | 2165 |
| gaa gaa aat ttg aac tgc ctt ggc cat tta agc act att att cat gag<br>Glu Glu Asn Leu Asn Cys Leu Gly His Leu Ser Thr Ile Ile His Glu<br>                715                    720                    725 | 2213 |
| gca aat gag gaa cag ggc aat agt atg atg aat ctt gat tgg agt tgg<br>Ala Asn Glu Glu Gln Gly Asn Ser Met Met Asn Leu Asp Trp Ser Trp<br>730                        735                    740 | 2261 |
| tta aca gaa tga<br>Leu Thr Glu<br>            745 | 2273 |

<210> SEQ ID NO 2
<211> LENGTH: 745
<212> TYPE: PRT
<213> ORGANISM: Homo sapiens

<400> SEQUENCE: 2

Met Glu Arg Pro Pro Gly Leu Arg Pro Gly Ala Gly Gly Pro Trp Glu
1               5                    10                   15

Met Arg Glu Arg Leu Gly Thr Gly Gly Phe Gly Asn Val Cys Leu Tyr
              20                    25                    30

Gln His Arg Glu Leu Asp Leu Lys Ile Ala Ile Lys Ser Cys Arg Leu
          35                    40                    45

Glu Leu Ser Thr Lys Asn Arg Glu Arg Trp Cys His Glu Ile Gln Ile
50                        55                    60

```
Met Lys Lys Leu Asn His Ala Asn Val Val Lys Ala Cys Asp Val Pro
 65                  70                  75                  80

Glu Glu Leu Asn Ile Leu Ile His Asp Val Pro Leu Leu Ala Met Glu
                 85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
130                 135                 140

Leu Lys Pro Glu Asn Ile Val Leu Gln Asp Val Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
305                 310                 315                 320

Ala Lys Ile Ile Ser Phe Leu Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
    370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480
```

```
Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
                580                 585                 590

Thr Val Gln Ser Gln Asp Arg Val Leu Lys Glu Arg Phe Gly His Leu
            595                 600                 605

Ser Lys Leu Leu Gly Cys Lys Gln Lys Ile Ile Asp Leu Leu Pro Lys
        610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
                660                 665                 670

Gly Ala Val Thr Pro Gln Ala Tyr Ala Trp Leu Ala Pro Asp Leu Ala
            675                 680                 685

Glu His Asp His Ser Leu Ser Cys Val Val Thr Pro Gln Asp Gly Glu
        690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735

Asn Leu Asp Trp Ser Trp Leu Thr Glu
                740                 745

<210> SEQ ID NO 3
<211> LENGTH: 8
<212> TYPE: PRT
<213> ORGANISM: Homo sapiens

<400> SEQUENCE: 3

Lys Ile Ile Asp Leu Leu Pro Lys
 1               5

<210> SEQ ID NO 4
<211> LENGTH: 18
<212> TYPE: PRT
<213> ORGANISM: Homo sapiens
<220> FEATURE:
<221> NAME/KEY: SITE
<222> LOCATION: (4)
<223> OTHER INFORMATION: /note=" Xaa is apartic acid or alanine (D/A)."
<221> NAME/KEY: SITE
<222> LOCATION: (17)
<223> OTHER INFORMATION: /note="Xaa is proline or glycine (P/G)."

<400> SEQUENCE: 4

Lys His Arg Xaa Leu Lys Pro Glu Asn Ile Val Leu Gln Asp Val Gly
 1               5                  10                  15
```

Xaa Lys

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
       Construct

<400> SEQUENCE: 5
ccccatatgt accagcatcg ggaa                                          24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
       Construct

<400> SEQUENCE: 6
tcaaccaatt gtcttgagct cccc                                          24

<210> SEQ ID NO 7
<211> LENGTH: 20
<212> TYPE: DNA
<213> ORGANISM: Homo sapiens

<400> SEQUENCE: 7
catggcacca tcgttctctg                                               20

<210> SEQ ID NO 8
<211> LENGTH: 25
<212> TYPE: DNA
<213> ORGANISM: Homo sapiens

<400> SEQUENCE: 8
ctcaaagagc tctggggcca gatac                                         25

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
       Construct

<400> SEQUENCE: 9
tccgagatct ggacgagc                                                 18

<210> SEQ ID NO 10
<211> LENGTH: 9
<212> TYPE: PRT
<213> ORGANISM: Homo sapiens

<400> SEQUENCE: 10

Lys Ile Ile Asp Leu Gly Tyr Ala Lys
 1               5

<210> SEQ ID NO 11
<211> LENGTH: 14
<212> TYPE: PRT
<213> ORGANISM: Homo sapiens
<220> FEATURE:

-continued

```
<221> NAME/KEY: SITE
<222> LOCATION: (8)
<223> OTHER INFORMATION: /note="Xaa is Methionine or Tyrosine (M/Y)."
<221> NAME/KEY: SITE
<222> LOCATION: (9)
<223> OTHER INFORMATION: /note="Xaa is Valine or Glycine (V/G)."
<221> NAME/KEY: SITE
<222> LOCATION: (10)
<223> OTHER INFORMATION: /note="Xaa is Threonine, Asparagine, Arginine or
      Glutamic acid (T/N/R/E)."
<221> NAME/KEY: SITE
<222> LOCATION: (14)
<223> OTHER INFORMATION: /note="Xaa is Histidine, Isoleucine or Serine
      (H/I/S)."
<221> NAME/KEY: SITE
<222> LOCATION: (2)
<223> OTHER INFORMATION: /note="Xaa is any amino acid."
<221> NAME/KEY: SITE
<222> LOCATION: (11)
<223> OTHER INFORMATION: /note="Xaa is Glycine or Asparagine (G/N)."

<400> SEQUENCE: 11

Lys Xaa Val His Ile Leu Asn Xaa Xaa Xaa Xaa Thr Ile Xaa
  1               5                  10

<210> SEQ ID NO 12
<211> LENGTH: 11
<212> TYPE: PRT
<213> ORGANISM: Homo sapiens
<220> FEATURE:
<221> NAME/KEY: SITE
<222> LOCATION: (2)..(3)
<223> OTHER INFORMATION: /note="Xaa is any amino acid."
<221> NAME/KEY: SITE
<222> LOCATION: (8)
<223> OTHER INFORMATION: /note="Xaa is Threonine or Alanine (T/A)."

<400> SEQUENCE: 12

Lys Xaa Xaa Ile Gln Gln Asp Xaa Gly Ile Pro
  1               5                  10

<210> SEQ ID NO 13
<211> LENGTH: 9
<212> TYPE: PRT
<213> ORGANISM: Homo sapiens
<220> FEATURE:
<221> NAME/KEY: SITE
<222> LOCATION: (2)
<223> OTHER INFORMATION: /note="Xaa is any amino acid."

<400> SEQUENCE: 13

Lys Xaa Arg Val Ile Tyr Thr Gln Leu
  1               5

<210> SEQ ID NO 14
<211> LENGTH: 2931
<212> TYPE: DNA
<213> ORGANISM: Homo sapiens
<220> FEATURE:
<221> NAME/KEY: CDS
<222> LOCATION: (36)..(2306)

<400> SEQUENCE: 14
cgcgtccctg ccgacagagt tagcacgaca tcagt atg agc tgg tca cct tcc        53
                                       Met Ser Trp Ser Pro Ser
                                         1               5 ctg aca acg cag aca tgc ggg gcc tgg gaa atg aaa gag cgc ctt ggg      101
Leu Thr Thr Gln Thr Cys Gly Ala Trp Glu Met Lys Glu Arg Leu Gly
            10                  15                  20 aca ggg gga ttt gga aat gtc atc cga tgg cac aat cag gaa aca ggt      149
```

```
                    -continued

Thr Gly Gly Phe Gly Asn Val Ile Arg Trp His Asn Gln Glu Thr Gly
        25                  30                  35 gag cag att gcc atc aag cag tgc cgg cag gag ctc agc ccc cgg aac        197
Glu Gln Ile Ala Ile Lys Gln Cys Arg Gln Glu Leu Ser Pro Arg Asn
        40                  45                  50 cga gag cgg tgg tgc ctg gag atc cag atc atg aga agg ctg acc cac        245
Arg Glu Arg Trp Cys Leu Glu Ile Gln Ile Met Arg Arg Leu Thr His
55                  60                  65                  70 ccc aat gtg gtg gct gcc cga gat gtc cct gag ggg atg cag aac ttg        293
Pro Asn Val Val Ala Ala Arg Asp Val Pro Glu Gly Met Gln Asn Leu
                75                  80                  85 gcg ccc aat gac ctg ccc ctg ctg gcc atg gag tac tgc caa gga gga        341
Ala Pro Asn Asp Leu Pro Leu Leu Ala Met Glu Tyr Cys Gln Gly Gly
            90                  95                 100 gat ctc cgg aag tac ctg aac cag ttt gag aac tgc tgt ggt ctg cgg        389
Asp Leu Arg Lys Tyr Leu Asn Gln Phe Glu Asn Cys Cys Gly Leu Arg
        105                 110                 115 gaa ggt gcc atc ctc acc ttg ctg agt gac att gcc tct gcg ctt aga        437
Glu Gly Ala Ile Leu Thr Leu Leu Ser Asp Ile Ala Ser Ala Leu Arg
    120                 125                 130 tac ctt cat gaa aac aga atc atc cat cgg gat cta aag cca gaa aac        485
Tyr Leu His Glu Asn Arg Ile Ile His Arg Asp Leu Lys Pro Glu Asn
135                 140                 145                 150 atc gtc ctg cag caa gga gaa cag agg tta ata cac aaa att att gac        533
Ile Val Leu Gln Gln Gly Glu Gln Arg Leu Ile His Lys Ile Ile Asp
                155                 160                 165 cta gga tat gcc aag gag ctg gat cag ggc agt ctt tgc aca tca ttc        581
Leu Gly Tyr Ala Lys Glu Leu Asp Gln Gly Ser Leu Cys Thr Ser Phe
            170                 175                 180 gtg ggg acc ctg cag tac ctg gcc cca gag cta ctg gag cag cag aag        629
Val Gly Thr Leu Gln Tyr Leu Ala Pro Glu Leu Leu Glu Gln Gln Lys
        185                 190                 195 tac aca gtg acc gtc gac tac tgg agc ttc ggc acc ctg gcc ttt gag        677
Tyr Thr Val Thr Val Asp Tyr Trp Ser Phe Gly Thr Leu Ala Phe Glu
    200                 205                 210 tgc atc acg ggc ttc cgg ccc ttc ctc ccc aac tgg cag ccc gtg cag        725
Cys Ile Thr Gly Phe Arg Pro Phe Leu Pro Asn Trp Gln Pro Val Gln
215                 220                 225                 230 tgg cat tca aaa gtg cgg cag aag agt gag gtg gac att gtt gtt agc        773
Trp His Ser Lys Val Arg Gln Lys Ser Glu Val Asp Ile Val Val Ser
                235                 240                 245 gaa gac ttg aat gga acg gtg aag ttt tca agc tct tta ccc tac ccc        821
Glu Asp Leu Asn Gly Thr Val Lys Phe Ser Ser Ser Leu Pro Tyr Pro
            250                 255                 260 aat aat ctt aac agt gtc ctg gct gag cga ctg gag aag tgg ctg caa        869
Asn Asn Leu Asn Ser Val Leu Ala Glu Arg Leu Glu Lys Trp Leu Gln
        265                 270                 275 ctg atg ctg atg tgg cac ccc cga cag agg ggc acg gat ccc acg tat        917
Leu Met Leu Met Trp His Pro Arg Gln Arg Gly Thr Asp Pro Thr Tyr
280                 285                 290 ggg ccc aat ggc tgc ttc aag gcc ctg gat gac atc tta aac tta aag        965
Gly Pro Asn Gly Cys Phe Lys Ala Leu Asp Asp Ile Leu Asn Leu Lys
295                 300                 305                 310 ctg gtt cat atc ttg aac atg gtc acg ggc acc atc cac acc tac cct       1013
Leu Val His Ile Leu Asn Met Val Thr Gly Thr Ile His Thr Tyr Pro
                315                 320                 325 gtg aca gag gat gag agt ctg cag agc ttg aag gcc aga atc caa cag       1061
Val Thr Glu Asp Glu Ser Leu Gln Ser Leu Lys Ala Arg Ile Gln Gln
            330                 335                 340
```

-continued

| | | |
|---|---|---|
| gac acg ggc atc cca gag gag gac cag gag ctg ctg cag gaa gcg ggc<br>Asp Thr Gly Ile Pro Glu Glu Asp Gln Glu Leu Leu Gln Glu Ala Gly<br>        345                  350                  355 | 1109 |
| ctg gcg ttg atc ccc gat aag cct gcc act cag tgt att tca gac ggc<br>Leu Ala Leu Ile Pro Asp Lys Pro Ala Thr Gln Cys Ile Ser Asp Gly<br>360                  365                  370 | 1157 |
| aag tta aat gag ggc cac aca ttg gac atg gat ctt gtt ttt ctc ttt<br>Lys Leu Asn Glu Gly His Thr Leu Asp Met Asp Leu Val Phe Leu Phe<br>375                  380                  385                  390 | 1205 |
| gac aac agt aaa atc acc tat gag act cag atc tcc cca cgg ccc caa<br>Asp Asn Ser Lys Ile Thr Tyr Glu Thr Gln Ile Ser Pro Arg Pro Gln<br>                395                  400                  405 | 1253 |
| cct gaa agt gtc agc tgt atc ctt caa gag ccc aag agg aat ctc gcc<br>Pro Glu Ser Val Ser Cys Ile Leu Gln Glu Pro Lys Arg Asn Leu Ala<br>410                  415                  420 | 1301 |
| ttc ttc cag ctg agg aag gtg tgg ggc cag gtc tgg cac agc atc cag<br>Phe Phe Gln Leu Arg Lys Val Trp Gly Gln Val Trp His Ser Ile Gln<br>                425                  430                  435 | 1349 |
| acc ctg aag gaa gat tgc aac cgg ctg cag cag gga cag cga gcc gcc<br>Thr Leu Lys Glu Asp Cys Asn Arg Leu Gln Gln Gly Gln Arg Ala Ala<br>440                  445                  450 | 1397 |
| atg atg aat ctc ctc cga aac aac agc tgc ctc tcc aaa atg aag aat<br>Met Met Asn Leu Leu Arg Asn Asn Ser Cys Leu Ser Lys Met Lys Asn<br>455                  460                  465                  470 | 1445 |
| tcc atg gct tcc atg tct cag cag ctc aag gcc aag ttg gat ttc ttc<br>Ser Met Ala Ser Met Ser Gln Gln Leu Lys Ala Lys Leu Asp Phe Phe<br>                475                  480                  485 | 1493 |
| aaa acc agc atc cag att gac ctg gag aag tac agc gag caa acc gag<br>Lys Thr Ser Ile Gln Ile Asp Leu Glu Lys Tyr Ser Glu Gln Thr Glu<br>                490                  495                  500 | 1541 |
| ttt ggg atc aca tca gat aaa ctg ctg ctg gcc tgg agg gaa atg gag<br>Phe Gly Ile Thr Ser Asp Lys Leu Leu Leu Ala Trp Arg Glu Met Glu<br>505                  510                  515 | 1589 |
| cag gct gtg gag ctc tgt ggg cgg gag aac gaa gtg aaa ctc ctg gta<br>Gln Ala Val Glu Leu Cys Gly Arg Glu Asn Glu Val Lys Leu Leu Val<br>520                  525                  530 | 1637 |
| gaa cgg atg atg gct ctg cag acc gac att gtg gac tta cag agg agc<br>Glu Arg Met Met Ala Leu Gln Thr Asp Ile Val Asp Leu Gln Arg Ser<br>535                  540                  545                  550 | 1685 |
| ccc atg ggc cgg aag cag ggg gga acg ctg gac gac cta gag gag caa<br>Pro Met Gly Arg Lys Gln Gly Gly Thr Leu Asp Asp Leu Glu Glu Gln<br>                555                  560                  565 | 1733 |
| gca agg gag ctg tac agg aga cta agg gaa aaa cct cga gac cag cga<br>Ala Arg Glu Leu Tyr Arg Arg Leu Arg Glu Lys Pro Arg Asp Gln Arg<br>570                  575                  580 | 1781 |
| act gag ggt gac agt cag gaa atg gta cgg ctg ctg ctt cag gca att<br>Thr Glu Gly Asp Ser Gln Glu Met Val Arg Leu Leu Leu Gln Ala Ile<br>                585                  590                  595 | 1829 |
| cag agc ttc gag aag aaa gtg cga gtg atc tat acg cag ctc agt aaa<br>Gln Ser Phe Glu Lys Lys Val Arg Val Ile Tyr Thr Gln Leu Ser Lys<br>600                  605                  610 | 1877 |
| act gtg gtt tgc aag cag aag gcg ctg gaa ctg ttg ccc aag gtg gaa<br>Thr Val Val Cys Lys Gln Lys Ala Leu Glu Leu Leu Pro Lys Val Glu<br>615                  620                  625                  630 | 1925 |
| gag gtg gtg agc tta atg aat gag gat gag aag act gtt gtc cgg ctg<br>Glu Val Val Ser Leu Met Asn Glu Asp Glu Lys Thr Val Val Arg Leu<br>                635                  640                  645 | 1973 |
| cag gag aag cgg cag aag gag ctc tgg aat ctc ctg aag att gct tgt<br>Gln Glu Lys Arg Gln Lys Glu Leu Trp Asn Leu Leu Lys Ile Ala Cys<br>650                  655                  660 | 2021 |

| | | | | | | | | | | | | | | | |
|---|---|---|---|---|---|---|---|---|---|---|---|---|---|---|---|
| agc | aag | gtc | cgt | ggt | cct | gtc | agt | gga | agc | ccg | gat | agc | atg | aat | gcc | 2069 |
| Ser | Lys | Val | Arg | Gly | Pro | Val | Ser | Gly | Ser | Pro | Asp | Ser | Met | Asn | Ala |
| | | 665 | | | | 670 | | | | 675 | | | | | |
| tct | cga | ctt | agc | cag | cct | ggg | cag | ctg | atg | tct | cag | ccc | tcc | acg | gcc | 2117 |
| Ser | Arg | Leu | Ser | Gln | Pro | Gly | Gln | Leu | Met | Ser | Gln | Pro | Ser | Thr | Ala |
| 680 | | | | | 685 | | | | | 690 | | | | | |
| tcc | aac | agc | tta | cct | gag | cca | gcc | aag | aag | agt | gaa | gaa | ctg | gtg | gct | 2165 |
| Ser | Asn | Ser | Leu | Pro | Glu | Pro | Ala | Lys | Lys | Ser | Glu | Glu | Leu | Val | Ala |
| 695 | | | | 700 | | | | 705 | | | | 710 | | | |
| gaa | gca | cat | aac | ctc | tgc | acc | ctg | cta | gaa | aat | gcc | ata | cag | gac | act | 2213 |
| Glu | Ala | His | Asn | Leu | Cys | Thr | Leu | Leu | Glu | Asn | Ala | Ile | Gln | Asp | Thr |
| | | | 715 | | | | 720 | | | | 725 | | | | |
| gtg | agg | gaa | caa | gac | cag | agt | ttc | acg | gcc | cta | gac | tgg | agc | tgg | tta | 2261 |
| Val | Arg | Glu | Gln | Asp | Gln | Ser | Phe | Thr | Ala | Leu | Asp | Trp | Ser | Trp | Leu |
| | 730 | | | | | 735 | | | | | 740 | | | | |
| cag | acg | gaa | gaa | gaa | gag | cac | agc | tgc | ctg | gag | cag | gcc | tca | tga | | 2306 |
| Gln | Thr | Glu | Glu | Glu | Glu | His | Ser | Cys | Leu | Glu | Gln | Ala | Ser | | |
| 745 | | | | | 750 | | | | | 755 | | | | | |

| | | |
|---|---|---|
| tgtgggggga ctcgaccccc tgacatgggg cagcccatag caggccttgt gcagtggggg | 2366 |
| gactcgaccc cctgacatgg ggctgcctgg agcaggccgc gtgacgtggg gctgcctggc | 2426 |
| cgtggctctc acatggtggt tcctgctgca ctgatggccc aggggtctct ggtatccaga | 2486 |
| tggagctctc gcttcctcag cagctgtgac tttcacccag gacccaggac gcagccctcc | 2546 |
| gtgggcactg ccggcgcctt gtctgcacac tggaggtcct ccattacaga ggcccagcgc | 2606 |
| acatcgctgg ccccacaaac gttcagggt acagccatgg cagctccttc ctctgccgtg | 2666 |
| agaaaagtgc ttggagtacg gtttgccaca cacgtgactg gacagtgtcc aattcaaatc | 2726 |
| tttcagggca gagtccgagc agcgcttggt gacagcctgt cctctcctgc tctccaaagg | 2786 |
| ccctgctccc tgtcctctct cactttacag cttgtgtttc ttctggattc agcttctcct | 2846 |
| aaacagacag tttaattata gttgcggcct ggccccatcc tcacttcctc tttttatttc | 2906 |
| actgctgcta aaattgtgtt tttac | 2931 |

<210> SEQ ID NO 15
<211> LENGTH: 756
<212> TYPE: PRT
<213> ORGANISM: Homo sapiens

<400> SEQUENCE: 15

Met Ser Trp Ser Pro Ser Leu Thr Thr Gln Thr Cys Gly Ala Trp Glu
 1               5                  10                  15

Met Lys Glu Arg Leu Gly Thr Gly Gly Phe Gly Asn Val Ile Arg Trp
            20                  25                  30

His Asn Gln Glu Thr Gly Glu Gln Ile Ala Ile Lys Gln Cys Arg Gln
        35                  40                  45

Glu Leu Ser Pro Arg Asn Arg Glu Arg Trp Cys Leu Glu Ile Gln Ile
    50                  55                  60

Met Arg Arg Leu Thr His Pro Asn Val Val Ala Ala Arg Asp Val Pro
65                  70                  75                  80

Glu Gly Met Gln Asn Leu Ala Pro Asn Asp Leu Pro Leu Leu Ala Met
                85                  90                  95

Glu Tyr Cys Gln Gly Gly Asp Leu Arg Lys Tyr Leu Asn Gln Phe Glu
            100                 105                 110

Asn Cys Cys Gly Leu Arg Glu Gly Ala Ile Leu Thr Leu Leu Ser Asp
        115                 120                 125

-continued

```
Ile Ala Ser Ala Leu Arg Tyr Leu His Glu Asn Arg Ile Ile His Arg
        130                 135                 140
Asp Leu Lys Pro Glu Asn Ile Val Leu Gln Gln Gly Glu Gln Arg Leu
145                 150                 155                 160
Ile His Lys Ile Ile Asp Leu Gly Tyr Ala Lys Glu Leu Asp Gln Gly
                165                 170                 175
Ser Leu Cys Thr Ser Phe Val Gly Thr Leu Gln Tyr Leu Ala Pro Glu
        180                 185                 190
Leu Leu Glu Gln Gln Lys Tyr Thr Val Thr Val Asp Tyr Trp Ser Phe
        195                 200                 205
Gly Thr Leu Ala Phe Glu Cys Ile Thr Gly Phe Arg Pro Phe Leu Pro
        210                 215                 220
Asn Trp Gln Pro Val Gln Trp His Ser Lys Val Arg Gln Lys Ser Glu
225                 230                 235                 240
Val Asp Ile Val Val Ser Glu Asp Leu Asn Gly Thr Val Lys Phe Ser
                245                 250                 255
Ser Ser Leu Pro Tyr Pro Asn Asn Leu Asn Ser Val Leu Ala Glu Arg
        260                 265                 270
Leu Glu Lys Trp Leu Gln Leu Met Leu Met Trp His Pro Arg Gln Arg
        275                 280                 285
Gly Thr Asp Pro Thr Tyr Gly Pro Asn Gly Cys Phe Lys Ala Leu Asp
        290                 295                 300
Asp Ile Leu Asn Leu Lys Leu Val His Ile Leu Asn Met Val Thr Gly
305                 310                 315                 320
Thr Ile His Thr Tyr Pro Val Thr Glu Asp Glu Ser Leu Gln Ser Leu
                325                 330                 335
Lys Ala Arg Ile Gln Gln Asp Thr Gly Ile Pro Glu Glu Asp Gln Glu
        340                 345                 350
Leu Leu Gln Glu Ala Gly Leu Ala Leu Ile Pro Asp Lys Pro Ala Thr
        355                 360                 365
Gln Cys Ile Ser Asp Gly Lys Leu Asn Glu Gly His Thr Leu Asp Met
        370                 375                 380
Asp Leu Val Phe Leu Phe Asp Asn Ser Lys Ile Thr Tyr Glu Thr Gln
385                 390                 395                 400
Ile Ser Pro Arg Pro Gln Pro Glu Ser Val Ser Cys Ile Leu Gln Glu
                405                 410                 415
Pro Lys Arg Asn Leu Ala Phe Phe Gln Leu Arg Lys Val Trp Gly Gln
        420                 425                 430
Val Trp His Ser Ile Gln Thr Leu Lys Glu Asp Cys Asn Arg Leu Gln
        435                 440                 445
Gln Gly Gln Arg Ala Ala Met Met Asn Leu Leu Arg Asn Asn Ser Cys
        450                 455                 460
Leu Ser Lys Met Lys Asn Ser Met Ala Ser Met Ser Gln Gln Leu Lys
465                 470                 475                 480
Ala Lys Leu Asp Phe Phe Lys Thr Ser Ile Gln Ile Asp Leu Glu Lys
                485                 490                 495
Tyr Ser Glu Gln Thr Glu Phe Gly Ile Thr Ser Asp Lys Leu Leu Leu
        500                 505                 510
Ala Trp Arg Glu Met Glu Gln Ala Val Glu Leu Cys Gly Arg Glu Asn
        515                 520                 525
Glu Val Lys Leu Leu Val Glu Arg Met Met Ala Leu Gln Thr Asp Ile
        530                 535                 540
Val Asp Leu Gln Arg Ser Pro Met Gly Arg Lys Gln Gly Gly Thr Leu
```

```
545                 550                 555                 560
Asp Asp Leu Glu Glu Gln Ala Arg Glu Leu Tyr Arg Arg Leu Arg Glu
                565                 570                 575

Lys Pro Arg Asp Gln Arg Thr Glu Gly Asp Ser Gln Glu Met Val Arg
            580                 585                 590

Leu Leu Leu Gln Ala Ile Gln Ser Phe Glu Lys Lys Val Arg Val Ile
        595                 600                 605

Tyr Thr Gln Leu Ser Lys Thr Val Cys Lys Gln Lys Ala Leu Glu
    610                 615                 620

Leu Leu Pro Lys Val Glu Val Val Ser Leu Met Asn Glu Asp Glu
625                 630                 635                 640

Lys Thr Val Val Arg Leu Gln Glu Lys Arg Gln Lys Glu Leu Trp Asn
                645                 650                 655

Leu Leu Lys Ile Ala Cys Ser Lys Val Arg Gly Pro Val Ser Gly Ser
            660                 665                 670

Pro Asp Ser Met Asn Ala Ser Arg Leu Ser Gln Pro Gly Gln Leu Met
        675                 680                 685

Ser Gln Pro Ser Thr Ala Ser Asn Ser Leu Pro Glu Pro Ala Lys Lys
    690                 695                 700

Ser Glu Glu Leu Val Ala Glu Ala His Asn Leu Cys Thr Leu Leu Glu
705                 710                 715                 720

Asn Ala Ile Gln Asp Thr Val Arg Glu Gln Asp Gln Ser Phe Thr Ala
                725                 730                 735

Leu Asp Trp Ser Trp Leu Gln Thr Glu Glu Glu His Ser Cys Leu
            740                 745                 750

Glu Gln Ala Ser
        755

<210> SEQ ID NO 16
<211> LENGTH: 91
<212> TYPE: DNA
<213> ORGANISM: Artificial Sequence
<220> FEATURE:
<223> OTHER INFORMATION: Description of Artificial Sequence:Synthetic
      Construct

<400> SEQUENCE: 16
agcttgcgcg tatggcttcg ggtcatcacc atcaccatca cggtgactac aaggacgacg    60
atgacaaagg tgacatcgaa ggtagaggtc a                                    91

<210> SEQ ID NO 17
<211> LENGTH: 15
<212> TYPE: PRT
<213> ORGANISM: Homo sapiens

<400> SEQUENCE: 17

Glu Arg Pro Pro Gly Leu Arg Pro Gly Ala Gly Gly Pro Trp Glu
  1               5                  10                  15

<210> SEQ ID NO 18
<211> LENGTH: 13
<212> TYPE: PRT
<213> ORGANISM: Homo sapiens

<400> SEQUENCE: 18

Thr Ile Ile His Glu Ala Trp Glu Glu Gln Gly Asn Ser
  1               5                  10
```

```
<210> SEQ ID NO 19
<211> LENGTH: 13
<212> TYPE: PRT
<213> ORGANISM: Homo sapiens

<400> SEQUENCE: 19

Ser Lys Val Arg Gly Pro Val Ser Gly Ser Pro Asp Ser
 1               5                  10

<210> SEQ ID NO 20
<211> LENGTH: 14
<212> TYPE: PRT
<213> ORGANISM: Homo sapiens
<220> FEATURE:
<221> NAME/KEY: SITE
<222> LOCATION: (2)
<223> OTHER INFORMATION: /note="Xaa is any amino acid."

<400> SEQUENCE: 20

Lys Xaa Glu Glu Val Val Ser Leu Met Asn Glu Asp Glu Lys
 1               5                  10
```